(12) United States Patent
Liemersdorf et al.

(10) Patent No.: US 8,858,779 B2
(45) Date of Patent: Oct. 14, 2014

(54) SOLID ELECTROLYTE SENSOR HAVING TWO PUMPING CELLS FOR MEASUREMENT OF NITROGEN OXIDES

(75) Inventors: Dirk Liemersdorf, Sachsenheim (DE); Benjamin Sillmann, Moehringen (DE); Berndt Cramer, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 233 days.

(21) Appl. No.: 13/508,586

(22) PCT Filed: Oct. 21, 2010

(86) PCT No.: PCT/EP2010/065865
§ 371 (c)(1), (2), (4) Date: Aug. 3, 2012

(87) PCT Pub. No.: WO2011/069733
PCT Pub. Date: Jun. 16, 2011

(65) Prior Publication Data
US 2012/0285838 A1    Nov. 15, 2012

(30) Foreign Application Priority Data
Dec. 9, 2009   (DE) .......................... 10 2009 047 697

(51) Int. Cl.
| | |
|---|---|
| *G01N 27/419* | (2006.01) |
| *G01N 27/409* | (2006.01) |
| *G01N 7/00* | (2006.01) |
| *G01N 27/406* | (2006.01) |
| *G01N 27/41* | (2006.01) |

(52) U.S. Cl.
CPC ............ *G01N 27/419* (2013.01); *G01N 27/409* (2013.01); *G01N 7/00* (2013.01); *G01N 27/406* (2013.01); *G01N 27/41* (2013.01)
USPC .......... 205/784; 204/424; 73/23.31; 73/23.32

(58) Field of Classification Search
CPC ....... G01N 7/00; G01N 27/41; G01N 27/406; G01N 27/407; G01N 21/408; G01N 21/409; G01N 21/419
USPC ....................... 204/421–429; 73/23.31, 23.32
See application file for complete search history.

(56) References Cited

U.S. PATENT DOCUMENTS

| | | | |
|---|---|---|---|
| 2004/0094416 A1 * | 5/2004 | Chen et al. .................... | 204/426 |
| 2005/0210657 A1 | 9/2005 | Nakagaki et al. | |
| 2011/0314898 A1 * | 12/2011 | Liemersdorf et al. ....... | 73/23.31 |

FOREIGN PATENT DOCUMENTS

| | | |
|---|---|---|
| CN | 1186238 | 7/1998 |
| CN | 1788197 | 6/2006 |

(Continued)

OTHER PUBLICATIONS

International Search Report, PCT International Application No. PCT/EP2010/065865, dated Jan. 25, 2011.

(Continued)

*Primary Examiner* — Jennifer Dieterle
(74) *Attorney, Agent, or Firm* — Kenyon & Kenyon LLP

(57) ABSTRACT

A method for detecting a proportion of at least one gas species in a measurement gas space. A sensor element is used, having an oxygen reduction pumping cell for concentration of the gas species, a pumping cell connected downstream of the oxygen reduction pumping cell having pumping electrodes, and a gas-tight chamber. A pumping electrode may be exposed to gas from the measurement gas space which has been concentrated by the oxygen reduction pumping cell. A further pumping electrode is disposed in the gas-tight chamber. At least one measuring electrode is further disposed in the gas-tight chamber. The oxygen reduction pumping cell and the pumping cell are galvanically isolated. The method includes an initialization phase, and an accumulation phase.

11 Claims, 15 Drawing Sheets

(56) References Cited

FOREIGN PATENT DOCUMENTS

| DE | 102008040314 | 1/2010 |
|---|---|---|
| DE | 102008044374 | 6/2010 |

OTHER PUBLICATIONS

Kato, N. et al., "Thick Film $ZrO_2$ NOx Sensor," *Sae Transactions, Journal of Engines*, vol. 105, sect. 3, pp. 446-451, 1996.

\* cited by examiner

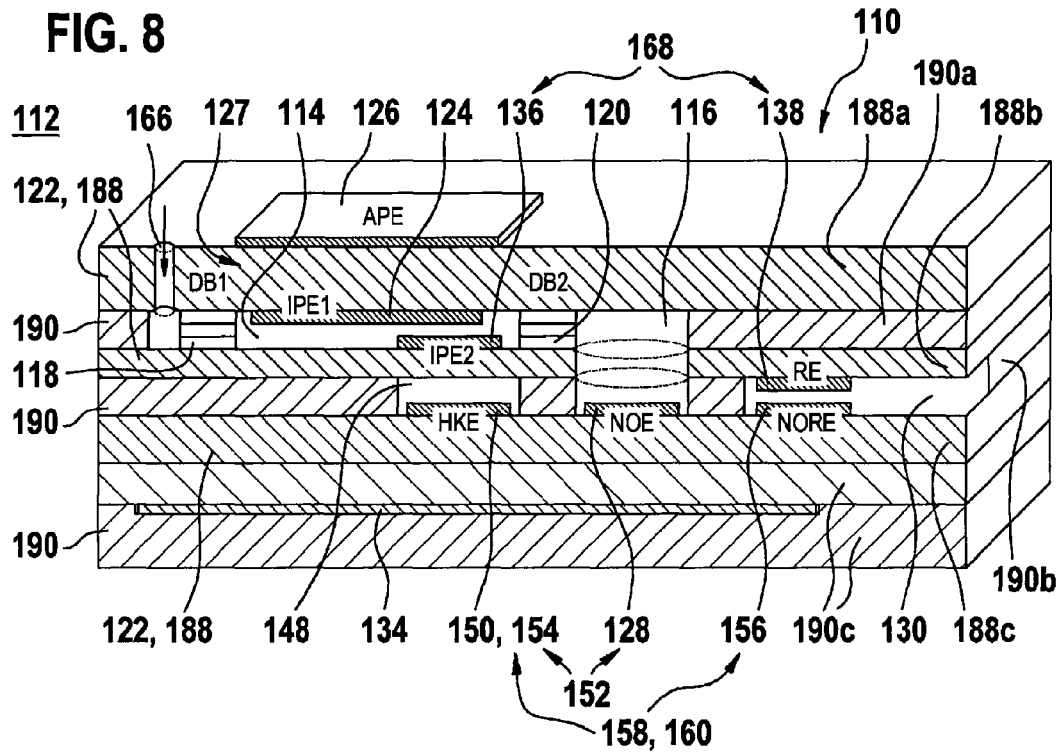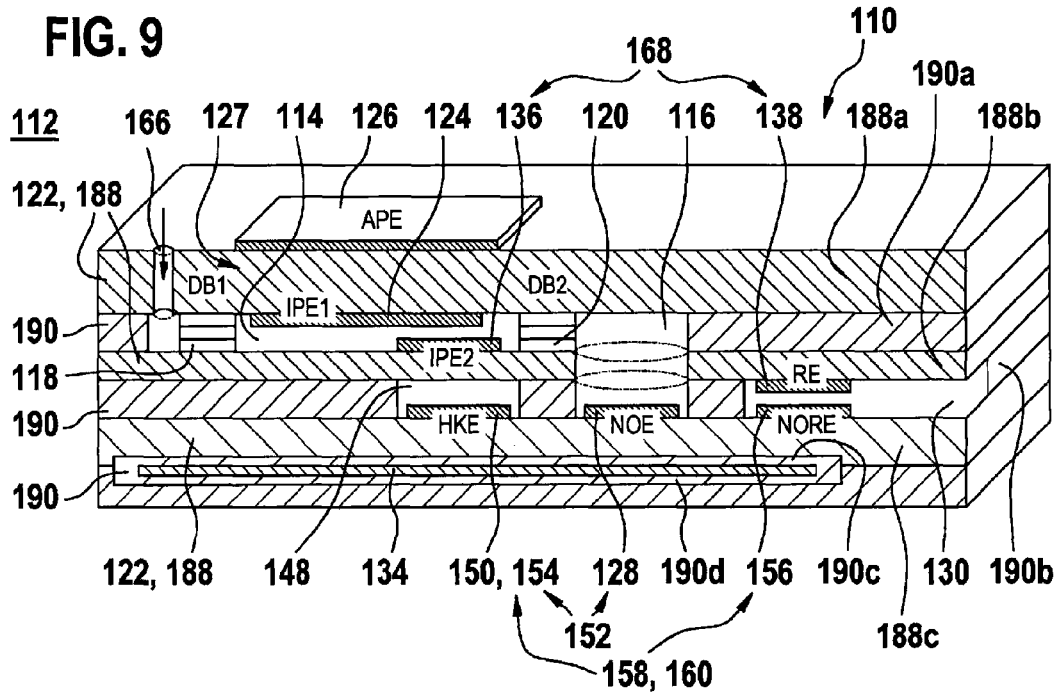

SOLID ELECTROLYTE SENSOR HAVING TWO PUMPING CELLS FOR MEASUREMENT OF NITROGEN OXIDES

BACKGROUND INFORMATION

As environmental legislation progresses, so the need grows for sensors with which even the smallest amounts of pollutants may be reliably determined. A major role is played in this context by, above all, measuring methods that enable the determination of gaseous pollutants in the ppm range. However, determination of the content of non-oxygen gases in particular, principally NOx (nitrogen oxides), in exhaust gases from combustion represents a particular challenge in this respect because of the oxygen fraction which is present at the same time. This is particularly important with regard to potential application as an on-board-diagnosis sensor (OBD sensor) for compliance with the coming exhaust gas legislation, since in that context limits will be laid down, for example for nitrogen oxides, that are below the resolution limit of currently available solid electrolyte gas sensors.

To measure small gas concentrations of non-oxygen exhaust gases, principally NOx, with an oxygen background present, use is made, in particular, of solid electrolyte sensors based on zirconium dioxide. In such sensors, there may be, for example, a plurality of sections or chambers which are separated from one another by diffusion barriers. Oxygen is removed at one or more first electrodes. Thus, ideally, oxygen is then no longer present in subsequent chambers, so that an electrode present in those chambers is then able to break down nitrogen oxides and pump the resulting oxygen as an ion current to a reference electrode or to another electrode. The very small electric current corresponding thereto is measured and is a measure, for example, of a nitrogen oxide concentration in the exhaust gas.

Sensor elements and methods for determining gas components in gas mixtures are described in German Patent Application Nos. DE 10 2008 040 314.8 and DE 10 2008 044 374.3. Described therein is a method for measuring a gas species in low concentration, in which accumulation of a quantity of oxygen equivalent to the concentration of the gas species to be measured is carried out by pumping into a gas-tight chamber with the aid of a pumping cell. A time interval until a characteristic concentration threshold of the accumulated gas is reached is determined. Then, a defined initial state is re-established in the gas-tight chamber by pumping.

A problem with the conventional methods and devices, however, is that the circuitry is generally very complex. In particular, for controlling the above-described method described in German Patent Application No. DE 10 2008 040 314.8 and DE 10 2008 044 374.3, to separate different functional cells of the sensor element it is necessary to use floating measuring devices for measuring voltage and current in order to avoid cross-talk between those functional cells.

SUMMARY

Accordingly, an example method and an example device are described which avoid the disadvantages of conventional methods and devices at least to a large extent. The example method may be carried out, in particular, using an example device according to the present invention, and/or the device may be configured to carry out a method according to the present invention. Accordingly, for possible embodiments of the device reference may be made to the description of the method and vice versa.

In a first example aspect of the present invention, a method for detecting a proportion of at least one gas species in a measurement gas space is proposed. The measurement gas space may be, for example, an exhaust system of an internal combustion engine. Accordingly, that measurement gas space may hold a gas, for example an exhaust gas. The expression "proportion of at least one gas species" may be understood as meaning, for example, an absolute percentage and/or a partial pressure of that gas species. The gas species may, in particular, be a gas species present in small quantities in the gas in the measurement gas space, for example a non-oxygen gas, especially an oxygen-containing gas compound, for example NOx and/or CO and/or $CO_2$.

At least one sensor element is used in the method. That sensor element includes at least one oxygen reduction pumping cell for concentration of the gas species. Concentration is generally to be understood in the context of the present invention as meaning a removal of at least one other gas species. This may result, for example, in the concentration of the gas species that is to be detected remaining at least approximately constant overall (for example apart from losses), for example expressed as a partial pressure and/or as mass per volume (for example $kg/m^3$) while the proportion of the gas species to be detected in the total gas mixture, however, increases. For example, a concentration ratio of the gas species to be detected in relation to other components of the gas mixture and/or a mole fraction of the gas species to be detected may increase. This concentration may be carried out especially by removing or at least reducing oxygen and/or another gas species present in the gas in the measurement gas space with the aid of an oxygen reduction pumping cell. Concentration may therefore also be understood especially as being a reduction of a specific gas species, for example oxygen.

In general, the present invention is described hereinafter generally with reference to oxygen-ion-conducting solid electrolytes, but without limitation of further possible embodiments. In that case, wherever "oxygen" is referred to in the context of the present invention, it is in fact the element oxygen that is meant, it being possible for the oxygen to exist in principle in various forms, for example as an ion or as molecular oxygen. It is also possible, however, for other types of solid electrolyte to be used. For example, it would be possible to use, as an alternative or in addition to oxygen-ion-conducting solid electrolytes, solid electrolytes that conduct other types of ion, for example proton conductors or nitrogen ion conductors. In that case, the term "oxygen" would have to be generally replaced by the corresponding element, for example by hydrogen when using proton conductors or by nitrogen when using nitrogen ion conductors.

Within the context of the present invention, a cell is generally to be understood as being a structure that includes at least two electrodes and at least one solid electrolyte connecting the electrodes. A solid electrolyte is to be understood within the context of the present invention as being a solid having ion-conducting properties. In particular, these may be oxygen-ion-conducting properties. Such solids are, for example, in the form of ceramics. For example, zirconium dioxides may be mentioned here, for example yttrium-stabilized zirconium dioxide (YSZ) and/or scandium-doped zirconium dioxide. It is also possible, however, for other solid electrolytes to be used in principle as an alternative or in addition.

With regard to the cells, a distinction is again made between pumping cells and measuring cells. Those types of cell do not, however, generally differ in their structure, but the designation "pumping" or "measuring" refers to a possible later use of those cells.

Accordingly, the oxygen reduction pumping cell may be constructed, for example, in such a manner that it has at least one chamber to which gas from the measurement gas space may be directly or indirectly admitted. For example, that at least one chamber may, as described in greater detail hereinafter, be in communication with the measurement gas space via at least one diffusion barrier which limits a further inflow of gas. The oxygen reduction pumping cell may accordingly have, for example, at least one inner pumping electrode disposed in the chamber, and at least one counter-electrode which is connected to the inner pumping electrode via at least one solid electrolyte. For example, that counter-electrode may be disposed in the measurement gas space or in another space, for example a surrounding space, so that, for example, oxygen or another type of gas that is to be removed may be removed from the chamber with the aid of the oxygen reduction pumping cell. It is also possible for a plurality of oxygen reduction pumping cells and/or a plurality of chambers of the mentioned kind to be provided, for example so as to be able to bring about cascaded removal of specific types of gas, such as, for example, oxygen, from the gas and in that manner provide a cascaded concentration of the gas species that is to be detected. The sensor element further has at least one pumping cell which is connected downstream of the oxygen reduction pumping cell and which has at least two pumping electrodes. The expression "connected downstream" is to be understood within the context of the present invention as meaning that gas that has already been concentrated may be admitted to the pumping cell. For example, a first pumping electrode of the two pumping electrodes of the pumping cell may be disposed in a second chamber which is connected downstream of the aforementioned chamber and which may be connected, for example, to the former chamber via at least one diffusion barrier or in a different manner. That first pumping electrode of the pumping cell will generally be referred to in the following description as a NO pumping electrode, without limitation of the possible gas species that are to be detected.

The sensor element further has at least one gas-tight chamber. While at least one of the pumping electrodes, namely the NO pumping electrode, may be exposed to the gas from the measurement gas space which has been concentrated by the oxygen reduction pumping cell, at least a second one of the pumping electrodes is disposed in the gas-tight chamber. A gas-tight chamber is generally to be understood within the context of the present invention as being a chamber that is sealed in such a manner that ingress of gas or gas components into the chamber or egress of gas or gas components from the chamber, apart from transport through a solid electrolyte, is completely prevented (gas-tight sealed chamber) or is at least slowed in such a manner that gas exchange between the interior of the gas-tight chamber and an area surrounding the chamber may be ignored in comparison with the other gas exchange processes that are of importance in the method, for example by being slowed by at least a factor of 100, especially by at least a factor of 1000. In particular, the gas exchange may be negligible on a time scale in which the phases of the method described in detail hereafter take place.

In addition, at least one measuring electrode is disposed in the gas-tight chamber. That measuring electrode may be a separate electrode which is separated from the pumping electrode disposed in the gas-tight chamber. As an alternative or in addition, the measuring electrode may be completely or partially combined with another electrode in the gas-tight chamber, for example with the pumping electrode disposed in the gas-tight chamber. As is described in greater detail below, the measuring electrode may form together with a reference electrode in a reference gas space, for example a reference air duct, a measuring cell.

The only element that has not been mentioned in connection with the cells described above, that is to say, the oxygen reduction pumping cell, the pumping cell and the optional measuring cell, is a solid electrolyte in each case, which connects the electrodes of those cells to one another. The solid electrolytes of the mentioned cells may be connected to one another, but preferably some or especially all of them are galvanically isolated from one another.

To solve the problems described above, especially to improve signal quality and with a view to simplifying the control used for the sensor element, according to an example embodiment of the present invention, at least the oxygen reduction pumping cell and the pumping cell are galvanically isolated from each other. Galvanic isolation is to be understood within the context of the present invention as meaning that the mentioned cells are not connected to one another via a solid electrolyte material. Thus, in particular, the above-described cells, that is, the oxygen reduction pumping cell and the pumping cell, may have solid electrolyte layers that are separated from one another, that is to say, especially solid electrolyte layers that do not have any ion-conducting connection between them. In general, therefore, the solid electrolytes of the cells galvanically isolated from one another should not be connected to one another in such a way that ion transport is possible from one of those solid electrolytes into the other or vice versa. For example, the solid electrolytes of the cells galvanically isolated from one another may be isolated from one another by at least one isolator material that eliminates ion transport at least to a large extent, for example that suppresses ion transport by at least a factor of 100, preferably by at least a factor of 1000 and most preferably by at least a factor of 10000. In addition, the solid electrolytes of the cells galvanically isolated from one another may optionally also be electrically isolated.

The electrodes of the above-described cells may be, in particular, metallic electrodes. In particular, those electrodes may include at least one noble metal such as, for example, platinum and/or palladium and/or gold. In particular, cermet electrodes may be used, that is to say, electrodes that have a ceramic component and a metal component. At the same time, one or more of the mentioned electrodes may have catalytic activity, that is, an activity capable of causing decomposition of gas components. Preferably, the inner pumping electrode of the oxygen reduction pumping cell is constructed to have a low catalytic activity in that case, so that preferably no decomposition or only slight decomposition takes place at that electrode. In that manner it is possible, for example, for pure oxygen to be conveyed out of the chamber. For example, a PtAu-cermet electrode may be used. Preferably, however, the NO pumping electrode of the pumping cell, that is, the pumping electrode that is exposed to concentrated gas from the measurement gas space, is constructed to have a higher catalytic activity. In that case, a PtRh-cermet electrode, for example, may be used.

The example method has the following phases, which are preferably carried out in succession. The phases may follow one another directly or other phases, not mentioned hereafter, may be provided. The phases described hereafter may be carried out in the order given or alternatively in a different order, for example in the reverse order. Furthermore, individual phases or a plurality of phases may be repeated, for example in an alternating method in which the method phases may be carried out in rotation. Exemplary embodiments will be described in greater detail below.

The example method includes at least one initialization phase. In the initialization phase, establishment or re-establishment of a defined initial state in the gas-tight chamber is carried out by pumping. That pumping may be performed, for example, by the at least one pumping cell mentioned above. As an alternative or in addition, however, at least one further pump may be provided which is specifically adapted and/or provided for the initialization phase. That at least one further pumping cell may be completely or partially identical to the pumping cell described above, but may also be constructed to be completely or partially separate from the pumping cell mentioned above. That further pumping cell, which may also be referred to as an initialization pumping cell, may include, for example, at least one initialization pumping electrode disposed inside the gas-tight chamber, which electrode may also be completely or partially identical to the at least one measuring electrode and/or completely or partially identical to the pumping electrode of the pumping cell disposed in the gas-tight chamber, which, however, may also be constructed as a separate initialization pumping electrode. A second initialization pumping electrode may be disposed outside the gas-tight chamber, for example in the measurement gas space and/or in a reference gas space, for example in the above-mentioned reference air duct.

A defined initial state is to be understood as meaning an at least approximately known composition and/or an otherwise known atmosphere in the interior of the gas-tight chamber. In particular, it may be a known concentration of oxygen and/or another gas component and/or a known partial pressure or absolute pressure of oxygen and/or another gas component. In particular, a defined initial state may be established or re-established by pumping the gas-tight chamber empty or at least to below a predefined pressure threshold or partial pressure threshold, especially in respect of oxygen and/or another gas component.

The example method further includes at least one accumulation phase. In the accumulation phase, accumulation of a quantity of oxygen in the gas-tight chamber is carried out by pumping via the pumping cell. The quantity of oxygen represents in this case a measure of a proportion of the gas species in the measurement gas. As mentioned above, that proportion may be an absolute concentration in per cent and/or may be a partial pressure. The expression "represents a measure of" is to be understood in the context of the present invention as meaning that the proportion of the gas species in the measurement gas space may be directly or indirectly inferred from the quantity of oxygen. This may be done, for example, on the basis of an empirical procedure, an analytical procedure or a semi-empirical procedure. For example, the quantity of oxygen in the gas-tight chamber may allow an inference to be made, by way of a known relationship and/or correlation curve and/or correlation table, regarding the gas species in the measurement gas, especially regarding a gas species that contains oxygen but which is different from molecular oxygen, such as, for example, NOx and/or CO and/or $CO_2$.

The initialization phase and/or the accumulation phase may be carried out in the proposed method especially for at least a predefined time period. That time period may be a fixed time period, for example in terms of an absolute length of that time period, or may be specified by at least one termination criterion, for example where one or more measured values reach at least one threshold. Exemplary embodiments will be described in greater detail below.

The proportion of the gas species is inferred in this case from a variation of the potential of the measuring electrode. The variation of the potential of the measuring electrode may be detected, for example, by way of a potential difference between the measuring electrode and at least one reference electrode. That reference electrode may, in particular, be disposed in at least one reference gas space. Instead of direct measurement of the potential variation of the measuring electrode, which in practice may be measured only with difficulty, there may therefore be detected as a measure of the potential variation a voltage variation of a Nernst voltage between the measuring electrode and the reference electrode, which is also intended to be included in the term potential variation for the purposes of the present invention. The detection of the potential variation may be carried out once or several times, for example during one or both of the above-mentioned phases and/or between the mentioned phases. As explained above, the reference gas space may, for example, be a sealed reference gas space in which a defined gas atmosphere exists or may be established at least during the period of the accumulation phase, for example in the form of a pumped reference and/or in the form of a reference gas duct which is in communication with an area surrounding the sensor element, for example with ambient air. The latter option is also referred to hereinafter as a reference air duct.

The inference made from the potential variation of the measuring electrode regarding the proportion of the gas species may be made in various ways. In particular, reference may be made in this respect to German Patent Application Nos. DE 10 2008 040 314.8 and DE 10 2008 044 374.3. Accordingly, for example, a time interval until the attainment of a characteristic concentration threshold of the accumulated gas may be determined. Then, for example, a defined initial state is re-established in the gas-tight chamber by pumping. From the time interval until the attainment of the characteristic concentration threshold it is possible to infer, for example, the proportion of the gas species that is to be detected. Accordingly, the determination of that time interval represents an exemplary embodiment of how the proportion of the gas species may be inferred from the potential variation of the measuring electrode during the initialization phase and/or the accumulation phase.

As an alternative or in addition, however, other methods are also possible for inferring the proportion of the gas species from the potential variation of the measuring electrode during the initialization phase and/or the accumulation phase. For example, the accumulation phase may be carried out, in particular, for a predefined time period of duration $\Delta t_{ACC}$, preferably a fixed duration $\Delta t_{ACC}$. The proportion of the gas species may be inferred in that case from the final value of the potential variation. For example, a final value of a Nernst voltage between the measuring electrode and the reference electrode may be detected at the end of the predefined time period, that is, after the elapse of duration $\Delta t_{ACC}$ after the beginning of the accumulation phase. For that purpose, a controller, for example, may be present, for example a controller in a device that includes the sensor element, which may include a voltage-measuring device.

As an alternative or in addition, once again a method may be carried out in which the accumulation phase is again carried out for a predefined time period of duration $\Delta t_{ACC}$, preferably of a fixed duration $\Delta t_{ACC}$. In this case, however, the potential variation, in particular the overall potential variation, is converted into at least one quantity that is characteristic of the potential variation, in which case the proportion of the gas species may be inferred from the characteristic quantity. That characteristic quantity may, for example, include one or more of the following characteristic quantities: an average value of the potential variation; an integral over the potential variation; an integral over a difference curve between the potential variation and a reference curve, preferably a reference curve having a constant function value. As explained above and as used within the context of the present invention altogether, the term potential variation may generally also include once again a potential difference, for example a Nernst voltage between the measuring electrode and a reference electrode.

In a further variant of the method, which again may similarly be carried out as an alternative or in addition, the initialization phase may be carried out for a predefined time period of a duration $\Delta t_{INI}$, preferably of a fixed duration $\Delta t_{INI}$. In this case, the proportion of the gas species may be inferred from the potential variation of the potential of the measuring electrode during the initialization phase. That inference may once again be made in various ways. For example, once again initial values of the potential variation, before the beginning of the initialization phase, may be included for the determination of the proportion of the gas species. As an alternative or in addition, once again it is possible to find from the potential variation itself, especially from the overall potential variation, at least one quantity that is characteristic of the potential variation, for example again an average value and/or an integral and/or an integral over a difference curve. In that manner, the proportion of the gas species may be inferred from the potential variation during the initialization phase. In the initialization phase, it is possible, in particular, for a current-controlled and/or charge-controlled, at least partial emptying of the gas-tight chamber to be carried out. A current-controlled emptying is to be understood as meaning an emptying in which a pumping current that is used for the emptying, for example a pumping current of an initialization pumping cell, follows a predefined current curve, for example a constant current curve. Accordingly, closed-loop current control, for example, may be provided. A device for detecting a proportion of at least one gas species may include, for example, a controller that arranges that current control, for example a closed-loop current control. As an alternative or in addition, a charge-controlled emptying may also take place, that is, an emptying in which an overall charge transported during an emptying operation follows a predefined curve. For that purpose, the device and/or the controller thereof may include, for example, a corresponding close-loop control system.

The potential variation may in this case be detected transiently, that is to say, by using continuous measurement and/or a plurality of instantaneous values capable of being associated with corresponding time values. The potential variation may then be evaluated, for example, with a trigger threshold evaluation and/or in an integral evaluation and/or a detection of a time period until attainment of a defined initial value that is to be attained for a subsequent accumulation phase.

As described above, the predefined time period—it also being possible to predefine a plurality of time periods—during which the initialization phase and/or the accumulation phase is carried out may be a fixed time period. Thus, for example, a fixed time period $\Delta t_{ACC}$ may be specified for the accumulation phase and/or a fixed time period $\Delta t_{INI}$ may be specified for the initialization phase. As an alternative or in addition, that at least one time period may, however, be variable. Thus, that at least one time period may include, for example, a time period until attainment of a termination criterion. For example, that termination criterion may be an attainment of a trigger threshold and/or a plurality of trigger thresholds. For example, a termination criterion may be met when a potential variation attains during the initialization phase and/or during the accumulation phase one or more predefined trigger thresholds.

In addition to the above-described example method in one or more of the described method variants, an example device for detecting a proportion of at least one gas species in a measurement gas space is also provided. The device may, in particular, be configured to carry out a method in accordance with one or more of the above-described method variants. Accordingly, the device may include, for example, at least one controller, the controller being configured to carry out a method in one or more of the described embodiments. That controller may, for example, include one or more voltage sources and/or one or more current sources and/or one or more voltage-measuring devices and/or one or more current-measuring devices. For example, a voltage source and/or a current source may be provided for acting upon the pumping cell, especially during the accumulation phase. As an alternative or in addition, at least one voltage source and/or at least one current source may be provided for acting upon the optional initialization pumping cell, especially during the initialization phase. Furthermore, at least one voltage-measuring device, for example, may be provided, especially a voltage-measuring device for measuring a Nernst voltage between the measuring electrode and the reference electrode. Once again as an alternative or in addition, the controller may also include, for example, at least one data-processing device, for example a data-processing device that is programmed to carry out a method in accordance with one or more of the above-described method variants. The controller may be completely or partially integrated in the above-described sensor element or may also be constructed to be completely or partially separate from the sensor element, for example in a separate device and/or an engine control unit.

As described above with reference to the method, the device includes at least one sensor element having at least one oxygen reduction pumping cell for concentration of the gas species and further includes at least one pumping cell which is connected downstream of the oxygen reduction pumping cell and which has at least two pumping electrodes. The sensor element further includes at least one gas-tight chamber, at least one of the pumping electrodes (NO pumping electrode) being exposable to gas from the measurement gas space which has been concentrated by the oxygen reduction pumping cell. At least a further one of the pumping electrodes is disposed in a gas-tight chamber. In addition, at least one measuring electrode is disposed in the gas-tight chamber. The oxygen reduction pumping cell and the pumping cell are galvanically isolated from each other.

The pumping electrode disposed in the gas-tight chamber and the measuring electrode may, as described above, be at least partially identical components or may be connected to each other. Alternatively, the pumping electrode disposed in the gas-tight chamber and the measuring electrode may, however, also be constructed to be completely or partially separate from each other.

The sensor element may, as described above, have at least one chamber for concentration of the gas species. In the chamber, at least one inner pumping electrode of the oxygen reduction pumping cell may be disposed. That inner pumping electrode will also be referred to hereinafter, without limitation of alternative possibilities for concentration, as an inner oxygen pumping electrode. The inner pumping electrode and the pumping electrode of the pumping cell which can be exposed to the concentrated gas from the measurement gas space (the NO pumping electrode) may also be electrically connected to each other in this case. That connection may be made inside the sensor element or may also be made outside the sensor element, for example with the aid of a shared electrical supply line inside the sensor element and/or outside the sensor element. That electrical connection becomes possible because the oxygen reduction pumping cell and the pumping cell are galvanically isolated from each other.

In the chamber for concentration of the gas species, at least one oxygen reduction measuring electrode may further be provided. As described above, the sensor element may further include at least one reference gas space, for example a reference air duct or another kind of reference gas space having a defined gas atmosphere. In the reference gas space, at least one oxygen reduction reference electrode may be provided. That oxygen reduction reference electrode may be completely or partially separate from the optional reference electrode described above, but may also be completely or partially identical to that reference electrode or may be electrically connected to that reference electrode. The oxygen reduction reference electrode and the oxygen reduction measuring electrode may together form at least one oxygen reduction measuring cell. An element that has not been mentioned is once again at least one possible solid electrolyte of that oxygen reduction measuring cell.

The oxygen reduction measuring cell may likewise be constructed to be galvanically isolated from the pumping cell. If that is the case, the measuring electrode may again be electrically connected to the inner pumping electrode of the oxygen reduction pumping cell and/or to the pumping electrode that may be exposed to the concentrated gas from the measurement gas space (the NO pumping electrode). That connection may be made, for example, once again analogously to the above description, by a shared supply line and/or a shared different kind of electrical connection which may be provided completely or partially inside the sensor element or alternatively completely or partially outside the sensor element.

As explained above, galvanic isolation means especially that the solid electrolytes of the cells galvanically isolated from one another are isolated with respect to one another, so that ion transport and preferably also electron transport from one solid electrolyte to the other is not possible. Thus, in particular, the oxygen reduction pumping cell and the pumping cell may each have solid electrolytes that are isolated with respect to one another. As described above, this may be accomplished, in particular, by the solid electrolytes being separated from one another by at least one isolator layer. That at least one isolator layer and/or a different isolator element for separating the solid electrolytes may include, for example, at least one aluminum oxide layer, since such a material may easily be integrated into a ceramic layered structure. Other types of isolator layer and/or isolator material may, however, also be used in principle.

As explained above, the sensor element may include at least one reference gas space, especially at least one reference air duct. As explained above, at least one reference electrode may be provided in the reference gas space, the reference electrode forming with the measuring electrode a measuring cell. The measuring cell also may be constructed to be galvanically isolated from the oxygen reduction pumping cell.

The example method and the example device, in accordance with the present invention, in one or more of the embodiments described above have numerous advantages over known methods and devices. For example, it is possible, in particular, for a signal quality of the measurements to be distinctly improved. The example device according to the present invention and the example method according to the present invention having a plurality of cells galvanically isolated from one another, especially a plurality of solid electrolytes isolated from one another, are considerably more accurate than conventional amperometric sensors and more accurate than the highly accurate accumulating principle. The example device according to the present invention and the example method according to the present invention combine both advantages of accumulating principle and galvanically isolated construction. Thus, an ohmic coupling of the cells may be completely or partly avoided. That enables a higher accuracy to be achieved since these cells which are galvanically isolated from one another are no longer able to interfere with one another by cross-talk. By using the accumulating principle in accordance with the foregoing description, it is possible to determine the signal, for example, by a time integration which is able to take place, in particular, inside the sensor and which is free of interference from the signal transmission of the extremely small signal currents.

BRIEF DESCRIPTION OF THE DRAWINGS

Exemplary embodiments of the present invention are illustrated in the Figures and are described in detail below.

FIG. 8 shows an exemplary embodiment of a sensor element of a device according to the present invention.

FIG. 9 shows an alternative exemplary embodiment to FIG. 8.

DETAILED DESCRIPTION OF EXAMPLE EMBODIMENTS

Figure 1:
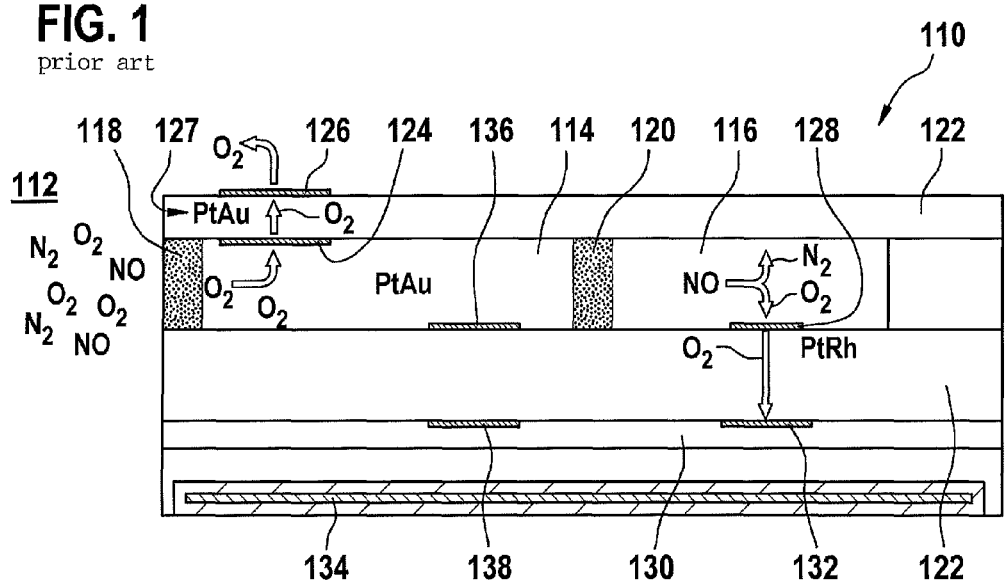
FIG. 1 is a sectional view of a conventional NOx limit current sensor.

In FIG. 1, a conventional sensor element 110 for determining a NOx concentration in a measurement gas space 112 is illustrated. It includes a plurality of chambers 114, 116 which are connected to measurement gas space 112 via diffusion barriers 118, 120. Sensor element 110 further includes a plurality of solid electrolyte layers 122, an inner oxygen pumping electrode 124 disposed in first chamber 114, an outer oxygen pumping electrode 126 disposed in measurement gas space 112, a NO pumping electrode 128 disposed in second chamber 116, and a NO counter-electrode 132 disposed in a reference air duct 130. In addition, a heating element 134 and further electrodes 136, 138 may also be provided in first chamber 114 and in reference air duct 130. For example, an oxygen reduction measuring electrode 136 may be provided in chamber 114, and an oxygen reduction reference electrode 138 may be provided in reference air duct 130, which electrodes may, however, also be completely or partially combined with other electrodes.

For measurement of small gas concentrations of non-oxygen gases, principally NOx, with an oxygen background present there are used, for example, sensor elements 110 of the kind shown in FIG. 1 based on $ZrO_2$. According to that principle, chambers 114—it also being possible for there to be a greater number of chambers—are provided which are separated from one another by diffusion barriers 120. Oxygen is removed at the inner oxygen pumping electrode 124. Accordingly, oxygen is then ideally no longer present. NO pumping electrode 128 then selectively decomposes NOx (which may include NO or other oxidation states) and pumps the resulting oxygen to NO counter-electrode 132, for example a reference electrode or another electrode. The very small electric current corresponding thereto, which is typically in the nanoampere to microampere range, is measured and represents a measure of the NO or NOx concentration in the exhaust gas. The electrodes of the layout of sensor element 110 shown in FIG. 1 may be adapted to their particular requirements. For example, it is possible to use the materials shown by way of example in FIG. 1, for example a platinum-gold alloy for electrodes 124 and 136 and a platinum-rhodium alloy for electrode 128.

Figure 2:
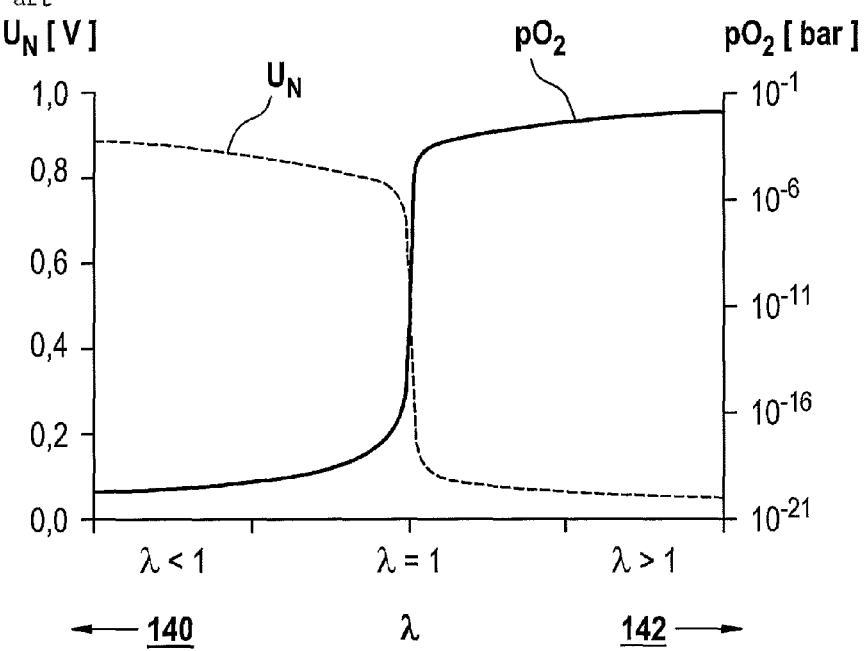
FIG. 2 shows a variation of a Nernst voltage of a gas-asymmetrical cell.

A characteristic curve, which is shown in FIG. 2, is obtained for the Nernst behavior of a gas-asymmetric cell having an electrode in the exhaust gas and an electrode in reference air duct 130, that is to say, a Nernst cell operating as a step-change probe. Entered on the horizontal axis is the relative fuel/air ratio $\lambda$, values where $\lambda<1$ characterizing a rich range 140 and values where $\lambda>1$ characterizing a lean range 142. On the left-hand vertical axis, the Nernst voltage $U_N$ is entered in Volt and, on the right-hand vertical axis, the oxygen partial pressure $pO_2$ is entered in bar. Near $\lambda=1$, a steep gradient of the curves will be seen, and consequently a clearer change in the Nernst voltage with little change in the oxygen content is to be observed in that region.

Figure 3:
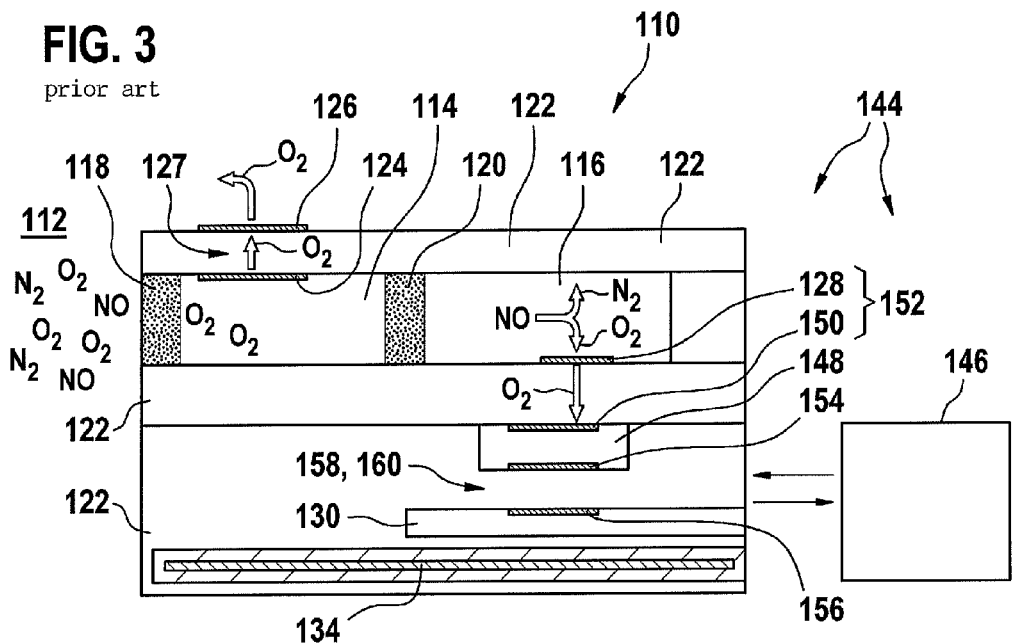
FIG. 3 shows an exemplary embodiment of a conventional device with galvanically coupled cells.

The layout of sensor element 110 shown in FIG. 1 has the disadvantages described above that, in particular, NOx concentrations are detectable only with difficulty. In contrast thereto, FIG. 3 shows a further configuration of a device 144 for detecting a proportion of a gas species in a measurement gas space 112, of the kind known, for example, in German Patent Application Nos. DE 10 2008 040 314.8 or DE 10 2008 044 374.3. Device 144 includes, in addition to a sensor element 110, whose layout will be explained below, a controller 146 which may include various electronic components and/or a data processing device and which is configured to carry out a method according to the invention together with sensor element 110.

Sensor element 110 is constructed substantially analogously to sensor element 110 in FIG. 1, and preferably has a plurality of solid electrolyte layers 122 and a plurality of chambers 114, 116 which are separated from one another by a diffusion barrier 120, first chamber 114 being in communication with the measurement gas space 112 via a further diffusion barrier 118. Furthermore, in this exemplary embodiment, once again an inner oxygen pumping electrode 124 is provided in first chamber 114, and an outer oxygen pumping electrode 126 is provided in measurement gas space 112 or in a space separated from that measurement gas space 112, for example a reference gas space. Inner oxygen pumping electrode 124 may, for example, once again include a PtAu-cermet electrode. Inner oxygen pumping electrode 124, outer oxygen pumping electrode 126 and solid electrolyte 122 form together an oxygen reduction pumping cell 127 which removes oxygen from chamber 114 and thereby concentrates the at least one gas species to be detected, for example NOx and/or CO.

In the exemplary embodiment illustrated, sensor element 110 further includes once again in second chamber 116 a NO pumping electrode 128 which may be exposed to concentrated gas from the measurement gas space and which is able to act as a first pumping electrode. That electrode forms, together with a first hollow-chamber electrode 150, which is disposed in a gas-tight chamber 148 and which is able to act as a second pumping electrode, and together with solid electrolyte 122, a pumping cell 152.

There is further provided in gas-tight chamber 148 in the exemplary embodiment illustrated a second hollow-chamber electrode 154 which may be constructed to be completely or partially identical to first hollow-chamber electrode 150, but which may alternatively, as indicated in FIG. 3, be in the form of a separate hollow-chamber electrode. That second hollow-chamber electrode 154 is capable of acting as a measuring electrode in the sense of the present invention described above.

In addition, once again a reference air duct 130 is provided which, for example, may be connected to a surrounding space, for example ambient air. Provided in that reference air duct 130 is a reference air electrode 156 which, for example, is capable of acting as a reference electrode in the sense of the foregoing description. Depending on the mode of operation, second hollow-chamber electrode 154, solid electrolyte 122 and reference air electrode 156 may form an initialization pumping cell 158 or a measuring cell 160.

In addition, once again a heating element 134 may be provided. In this simplest variant, therefore, sensor element 110 is constructed to have a gas-tight chamber 148. The latter may, for example, be in the form of a hollow space or in the form of a chamber filled with a porous, gas-permeable material. That gas-tight chamber 148 is separated by solid electrolyte 122, for example yttrium-stabilized zirconium dioxide, YSZ, which acts as an oxygen ion conductor, from the gas of measurement gas space 112, for example an exhaust gas. Oxygen may be pumped into gas-tight chamber 148 via pumping cell 152. The at least one reference air electrode 156 is disposed in reference air duct 130 which, for example, may be in communication with the outside air environment containing about 21% $O_2$. As described above, depending on the embodiment, hollow-chamber electrodes 150, 154 may also be completely or partially combined or the functionality of those electrodes may be replaced by a single hollow-chamber electrode. In that manner it is possible to reduce the number of electrodes. To obtain an adequate ion conductivity of solid electrolyte 122, sensor element 110 is preferably adjusted to the appropriate operating temperature by internal heating element 134.

For the mode of operation of sensor element 110 illustrated in FIG. 3, reference may be made, for example, to German Patent Application Nos. DE 10 2008 044 374.3 and DE 10 2008 040 314.8 described above. By way of oxygen pumping electrodes 124, 126, concentration of the gas species to be detected, for example NOx and/or CO and/or $CO_2$, takes place. That gas species, which preferably contains oxygen, is decomposed at NO pumping electrode 128 which preferably exhibits catalytic activity. Oxygen may then be pumped into gas-tight chamber 148 via pumping cell 152. This may be accomplished either by an active pumping process, that is to say, by impressing a voltage and/or current function, or passively by loading pumping cell 152 via an ohmic resistance. The latter is also referred to as an autonomous pumping cell.

For quantitative determination of the gas species that is to be detected (e.g. NOx, CO etc.) selectively pumping electrode materials are preferably used, especially for NO pumping electrode 128. Alternatively or in addition, the selectivity may also be assisted by an electrochemically assisted pumping process, for example with a characteristic decomposition voltage of oxygen-containing gases. In addition, as shown in FIG. 3, the oxygen present in the exhaust gas may be removed in an upstream, diffusion-limited first chamber 114 with the aid of a selective oxygen pumping cell, preferably having lower catalytic activity, for example a AuPt-cermet electrode.

It is pointed out that sensor layout 112 shown in FIG. 3 may be modified in various ways. For example, cascaded oxygen removal may be carried out, also with more than two oxygen reduction chambers 114. Furthermore, the layout illustrated in FIG. 3 may also be modified by variation of the arrangement of the various chambers 114, 116 and 148 and of the arrangement of reference air duct 130. Thus, it is possible, for example, to implement various horizontal and/or vertical arrangements of those individual chambers. In addition, a reduction and/or variation of the number of electrodes is possible, for example, as already mentioned in part above, by amalgamating and/or at least partially combining one or more of the electrodes shown in FIG. 3.

Figure 4:
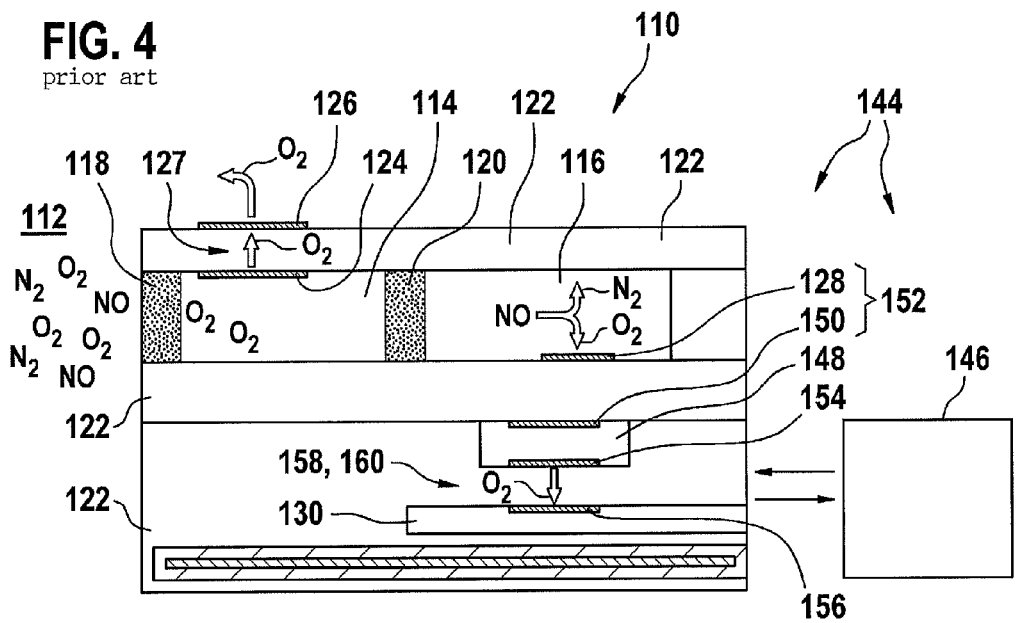
FIG. 4 shows the device shown in FIG. 3, during an initialization phase.
Figure 5:
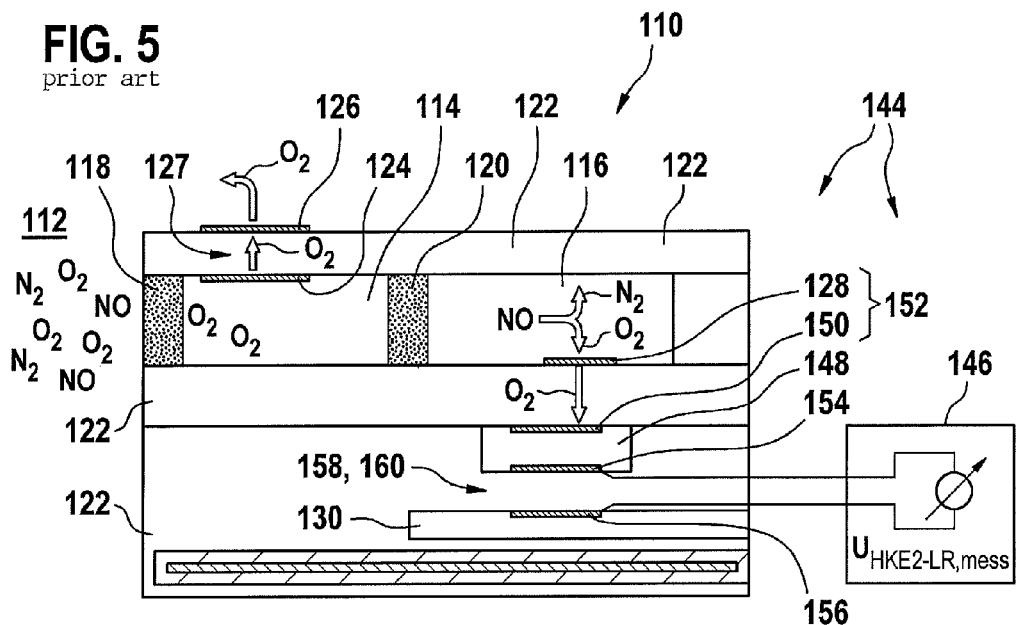
FIG. 5 shows the device shown in FIG. 3, during an accumulation phase.

The example method includes two phases, which is described in detail below with reference to FIGS. 4 and 5. FIG. 4 illustrates an initialization phase, and FIG. 5 an accumulation phase. During the accumulation phase, a quantity of oxygen correlated, for example, with the NOx concentration or a concentration of another kind of gas species to be detected is collected in gas-tight chamber 148 which is separated from the exhaust gas in measurement gas chamber 112, by a pumping process, that is, for example, actively by impressing a pumping voltage and/or a pumping current on pumping cell 152 and/or passively in the form of an autonomous pumping cell. Before each new cycle, in the initialization process illustrated in FIG. 4 that gas-tight chamber 148 is preferably pumped empty or otherwise brought into a defined initial state. As soon as the accumulation process shown in FIG. 5 begins, oxygen, correlated with the NOx concentration, is transported into gas-tight chamber 148, namely by pumping cell 152, and accumulates in gas-tight chamber 148.

In the initialization phase illustrated in FIG. 4, a defined initial state is established, for example by a voltage- or current-controlled pumping process via electrodes 154 and 156 and intervening solid electrolyte 122 which cooperate as an initialization pumping cell 158 in that initialization phase. The associated measured variable of the chamber state in gas-tight chamber 148 is the Nernst voltage between second hollow-chamber electrode 154 and reference air electrode 156, which is also referred to hereinafter as $U_{HKE2-LR,measure}$.

In the accumulation phase, by application of a pumping voltage/current to pumping cell 152 the oxygen obtained from the NO decomposition (or the decomposition of another kind of oxygen-containing gas component), which is correlated with the NOx concentration, is pumped into gas-tight chamber 148 acting as an accumulation chamber. Consequently, the $O_2$ concentration in gas-tight chamber 148 increases.

The evaluation of the chamber state, that is, its oxygen content, is carried out, for example, by measuring a Nernst voltage between electrodes 154 and 156. In this case, the cell formed by electrodes 154, 156 and intervening solid electrolyte 122 acts as a measuring cell 160. Second hollow-chamber electrode 154 acts in this case as a measuring electrode. The Nernst voltage of measuring cell 160 correlates with the oxygen content in gas-tight chamber 148 acting as an accumulation chamber.

Figure 6:
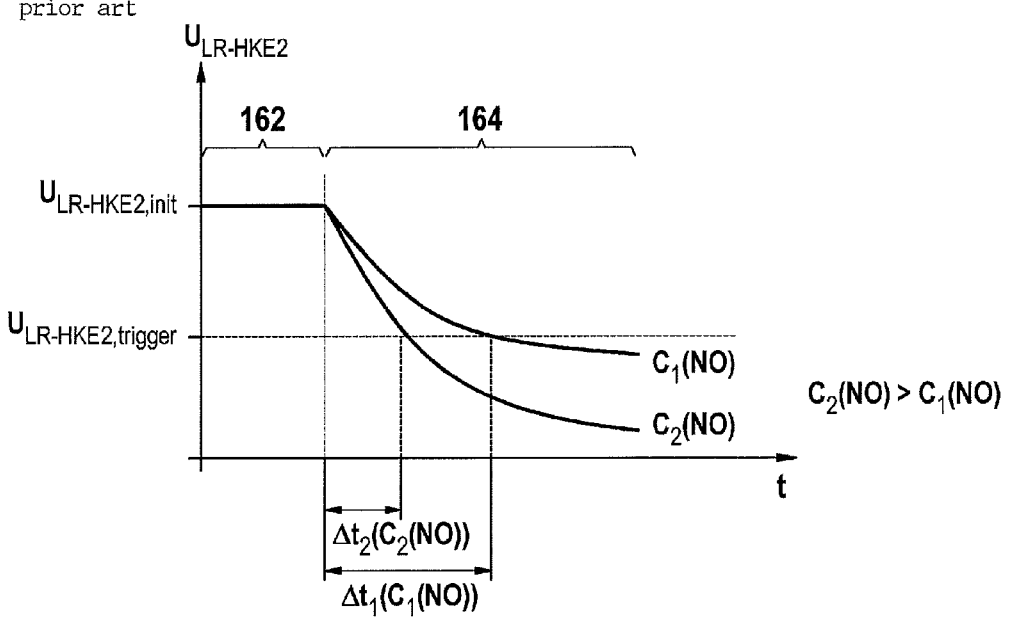
FIG. 6 shows a conventional method for determining a NOx concentration.

In the case of the methods described in German Patent Application Nos. DE 10 2008 044 374.3 and DE 10 2008 040 314.8, a variation of Nernst voltage $U_{LR-HKE2}$ described, for example, in FIG. 6 results, which variation is illustrated in FIG. 6. In that illustration, the initialization phase is identified by reference numeral 162 and the accumulation phase by reference numeral 164. The measured variable in this method known from the post-published related art is the time period $\Delta t$ needed to attain a defined threshold value $U_{LR-HKE2,trigger}$ of Nernst voltage $U_{LR-HKE2}$ which falls with increasing oxygen concentration. FIG. 6 shows two different NO concentrations, concentration $C_2(NO)$ being greater than concentration $C_1(NO)$. As the NO concentration increases, gas-tight chamber 148 is filled more rapidly, and a rapid drop in the voltages between second hollow-chamber electrode 154 and reference air electrode 156 results.

As an alternative or in addition to the method described in FIG. 6, a large number of other methods may be implemented with which the proportion of the gas species to be detected in the measurement gas space 112 may be inferred from the potential variation of second hollow-chamber electrode 154, acting as a measuring electrode, during the initialization phase and/or the accumulation phase. In this regard, reference may be made, for example, to the foregoing description.

Figure 7:
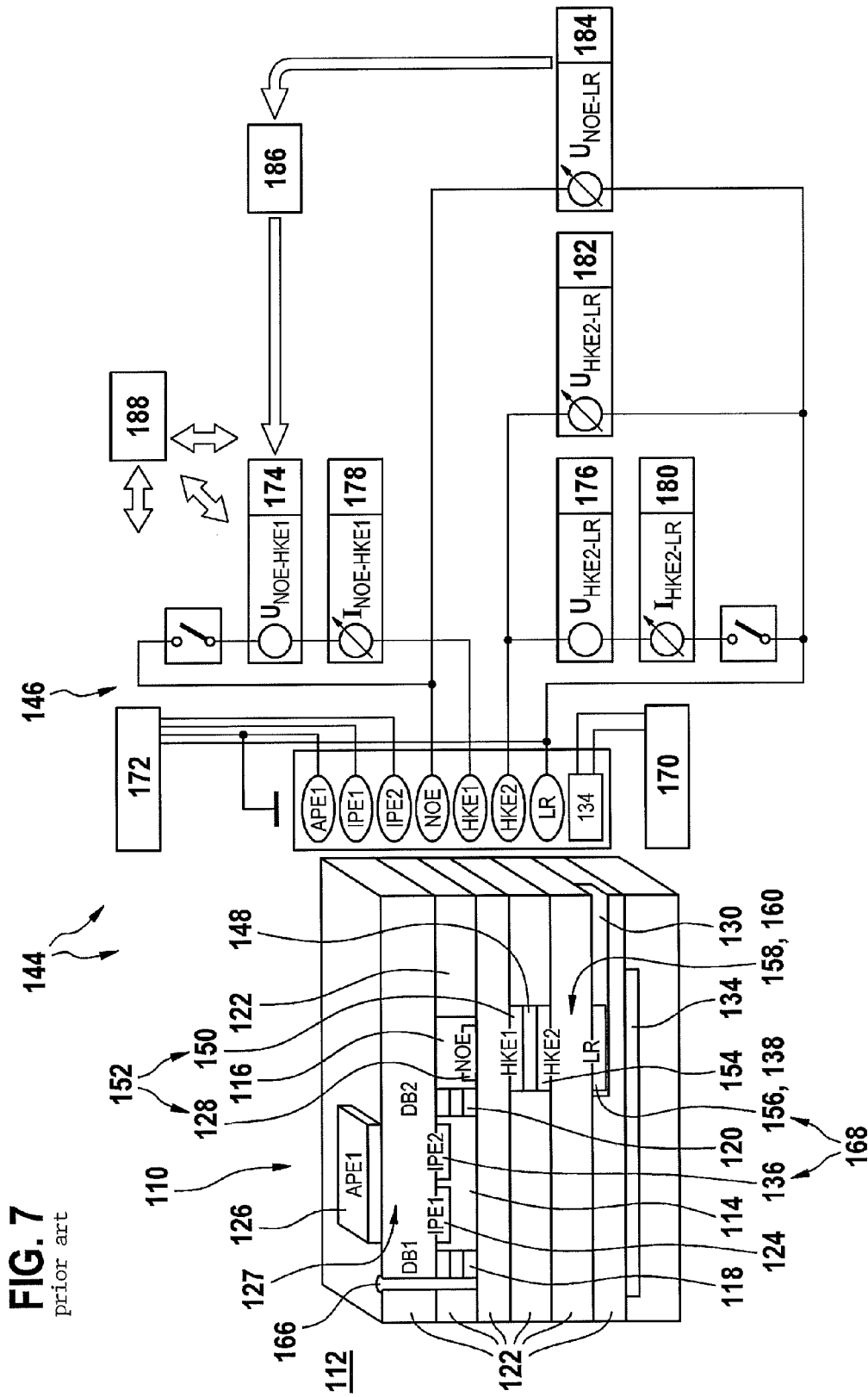
FIG. 7 shows a schematic measuring arrangement of a device for carrying out the described method using the conventional device shown in FIG. 3 with galvanically coupled cells.

FIG. 7 illustrates an exemplary embodiment of a device 144, also illustrating schematically details of a possible configuration of controller 146. FIG. 7 show a conventional device as could be used, for example, to implement the method described in German Patent Application Nos. DE 10 2008 044 374.3 or DE 10 2008 040 314.8. Device 144 accordingly includes a sensor element 110 which could be constructed, for example, analogously to sensor element 110 in FIG. 3. Reference may accordingly be made in large part to the description of FIG. 3. For example, sensor element 110 illustrated in FIG. 3 could also be used in device 144 shown in FIG. 7. The sensor element 110 actually illustrated in FIG. 7 does not have a gas inlet at the end face as in the schematic illustration shown in FIG. 3 (which could also be of a different construction), but has a gas inlet bore 166.

A further difference to be noted is that, in the exemplary embodiment illustrated, an oxygen reduction measuring electrode 136 is furthermore provided in first chamber 114. Oxygen reduction measuring electrode 136 forms together with solid electrolyte 122 and reference air electrode 156 in reference air duct 130 an oxygen reduction measuring cell 168. In the exemplary embodiment illustrated, only one electrode is provided in reference air duct 130. Alternatively, a plurality of electrodes could also be provided, for example by providing an oxygen reduction reference electrode 138 in addition to reference air electrode 156, analogously to the exemplary embodiment in FIG. 1.

The electrodes are designated in FIG. 7 as follows:
outer oxygen pumping electrode 126: APE1
inner oxygen pumping electrode 124: IPEI
oxygen reduction measuring electrode 136: IPEII
first pumping electrode, NO pumping electrode 128: NOE
second pumping electrode, first hollow-chamber electrode 150: HKEI
measuring electrode, second hollow-chamber electrode 154: HKEII
reference air electrode 156: LR Since, in accordance with the conventional sensor design of sensor element 110 still shown in FIG. 7, all the electrodes are connected to one another via an ion-conducting solid electrolyte 122, in order to separate the different functional cells it is necessary to use floating sources and floating measuring devices for measuring current and/or voltage. This is illustrated in the conventional controller 146 in FIG. 7. Therein, the following reference numerals denote the following elements:

170: heater supply for supplying heating element 134,
172: operating and evaluating circuit $O_2$ removal
174, 176: floating voltage sources
178, 180: floating current-measuring devices
182, 184: floating voltage-measuring devices,
186: a closed-loop controller, and
188: a microcontroller.

Altogether, the effort that has to be invested in controller 146—the complexity of that controller 146 is relatively high—involves corresponding costs. A controller 146 is generally understood within the context of the present invention to be a driving and evaluating circuit which is capable of controlling at least parts of the functionalities of device 144, and which is capable, for example, of providing corresponding voltages and/or currents, and which is capable, for example, of measuring corresponding voltages and/or currents in order to carry out one or more of the method variants described above.

FIGS. 8 and 9 show, by contrast, example embodiments according to the present invention of sensor elements 110, which embodiments may be used in place of sensor element 110 in a device 144, for example in a device 144 shown in FIG. 7 or in a simplified device which will be described in greater detail below. In contrast to sensor element 110 shown in FIG. 7, the sensor elements shown in FIG. 8 do not have a single, continuous solid electrolyte 122 or a plurality of solid electrolytes 122 connected to one another in an ion-conducting manner but have a plurality of solid electrolyte layers 188. FIGS. 8 and 9 each show as examples three such solid electrolyte layers 188 identified by letters 188a, 188b and 188c. In the exemplary embodiments according to the present invention in FIGS. 8 and 9, solid electrolyte layers 188a through 188c are separated from one another by isolator layers 190. FIG. 8 illustrates by way of example three isolator layers designated 190a, 190b and 190c whereas, in FIG. 9, by way of example isolator layers 190a, 190b, 190c and 190d are provided. In the exemplary embodiment shown in FIG. 8, heating element 134 is embedded in isolator layers 190c whereas, in FIG. 9, embedding into solid electrolyte layers 188 between isolator layers 190c and 190d is performed. The exemplary embodiments in FIGS. 8 and 9 are otherwise comparable, however.

Furthermore, instead of a single electrode in reference air duct 130, in both exemplary embodiments shown in FIG. 8 and FIG. 9 optionally a plurality of such electrodes are provided, namely an oxygen reduction reference electrode 138, also designated RE, and a reference air electrode 146, also designated NORE. Oxygen reduction reference electrode 138 and an oxygen reduction measuring electrode 136 disposed in first chamber 114 are in this case connected via a shared solid electrolyte layer 188 and form the oxygen reduction measuring cell already described above.

Furthermore, in this exemplary embodiment, optionally only a single electrode is provided in gas-tight chamber 148, which electrode is generally designated HKE here. That electrode assumes simultaneously the function of first hollow-chamber electrode 150 acting as the second pumping electrode and the function of second hollow-chamber electrode 154 acting as the hollow-chamber measuring electrode. A different configuration, for example a multi-part configuration, of that electrode is also possible in principle. In the exemplary embodiment illustrated, the shared hollow-chamber electrode is generally designated HKE. HKE forms together with the NO pumping electrode (designated NOE in FIG. 9) pumping cell 152 and, together with NORE, measuring cell 160.

Owing to the use of isolator layers 190, in the illustrated exemplary embodiment oxygen reduction pumping cell 127 and cells 152, 160 are galvanically isolated from one another. That galvanic isolation may be used inter alia to reduce the number of supply lines in the sensor structure in FIGS. 8 and 9. The galvanic isolation of electrochemical cells 127 and 152, 160 may be effected by using non-oxygen-ion-conducting intermediate layers, which are generally referred to, as described above, as isolator layers 190. Those isolator layers 190 accordingly have only a low ion conductivity. Optionally, they may additionally have a low electrical conductivity, which, however, is only of minor importance in the context of the present invention. There may be used as isolator layers 190, for example, aluminum oxide layers which may be in the form of both films and printed layers. Operation of gas-tight chamber 148, which acts as an accumulation chamber, is implemented merely by HKE 150, 154.

It should be pointed out that, as mentioned above, reference air duct 130 may also be implemented in a different manner. For example, it may be completely or partially replaced by a different reference space, for example by a so-called pumped reference.

Owing to the galvanic isolation of electrochemical cells 127 and 152, 160, electrodes IPE I, IPE II and NOE may be completely or partially electrically connected to one another, which may preferably already be done within the sensor element. In that manner it is possible to use, for example, a shared connection (SC). That procedure makes it possible to save on two supply lines of the sensor element. Furthermore, the structure in FIGS. 8 and 9 for the integrative ceramic NOx sensor with closed accumulation chamber, especially in combination with the electrical circuitry and evaluation circuit yet to be described hereinafter (see, for example, FIG. 10), provides the possibility of completely dispensing with floating sources and floating measuring devices.

Figure 10:
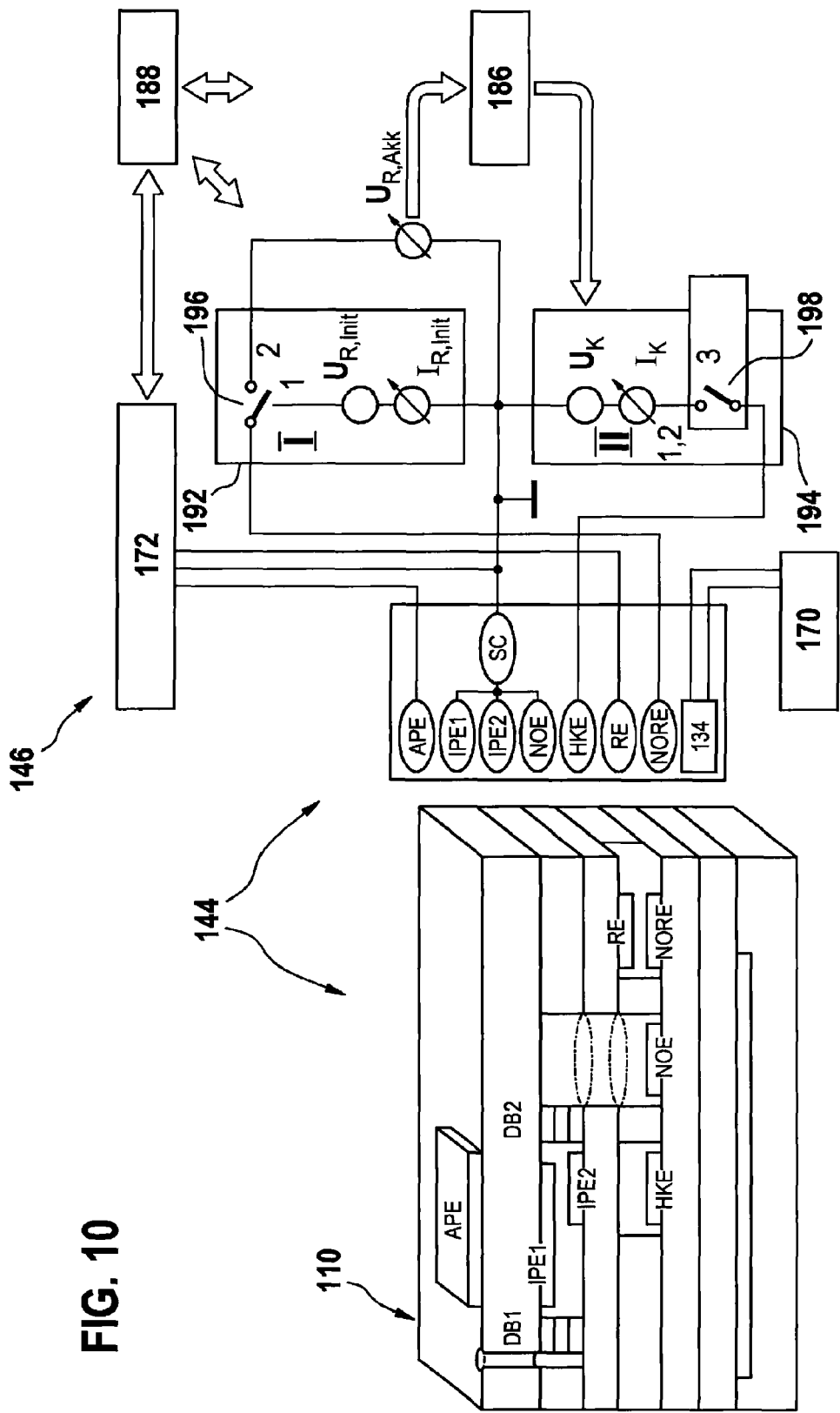
FIG. 10 shows a schematic representation of a device according to the present invention having a sensor element as shown in FIG. 8.

In FIG. 10, a device 144 according to the present invention is illustrated in an exemplary embodiment. That illustration also shows schematically an exemplary embodiment of a simplified controller 146, with reference to which the simplifications as compared with controller 146 shown in FIG. 7 will be explained. By way of example, FIG. 10 shows a sensor element 110 analogous to the exemplary embodiment in FIG. 8. It is also possible, however, to use other types of sensor element 110 with cells galvanically isolated from one another.

For a description of the elements of controller 146 illustrated in FIG. 10 reference may be made in large part to the description of FIG. 7. Owing to the galvanic isolation of oxygen reduction pumping cell 127, oxygen reduction measuring cell 168 and cells 152, 160 by isolator layers 190 it is possible, however, as mentioned above, for electrodes IPE I, IPE II and NOE to have a shared connection, as is illustrated in FIG. 10 by the symbol "SC". In that manner, not only is it possible to save on supply lines but it is also possible for the electrical devices shown in FIG. 7, for example voltage sources 174, 176, current-measuring devices 178, 180 and voltage-measuring devices 182, 184, to be partially combined, to be of a non-floating construction and to be altogether greatly simplified. In that case, as explained in FIG. 10, combination elements 192, 194 are used, which may include voltage and/or current sources and voltage-measuring and/or current-measuring devices. In addition, first combination element 192 includes a switch 196 and, as illustrated in FIG. 10, second combination element 194 may optionally also include a switch 198.

Figure 11A:
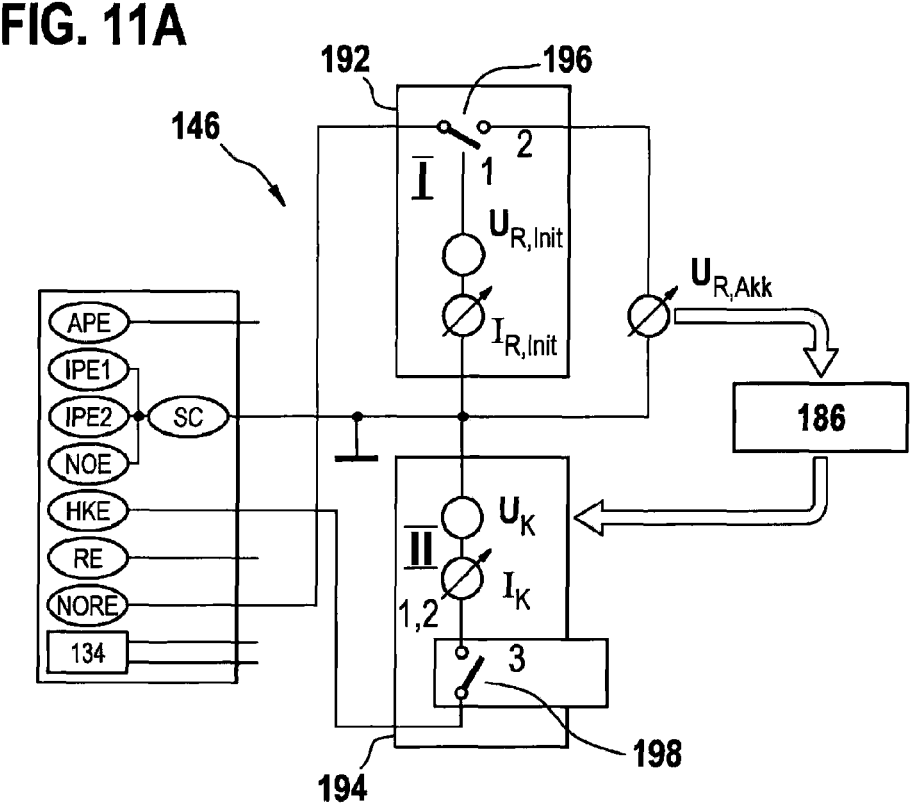
FIGS. 11A and 11B show simplified subcomponents of the controller of the device shown in FIG. 10, in two different configurations.
Figure 11B:
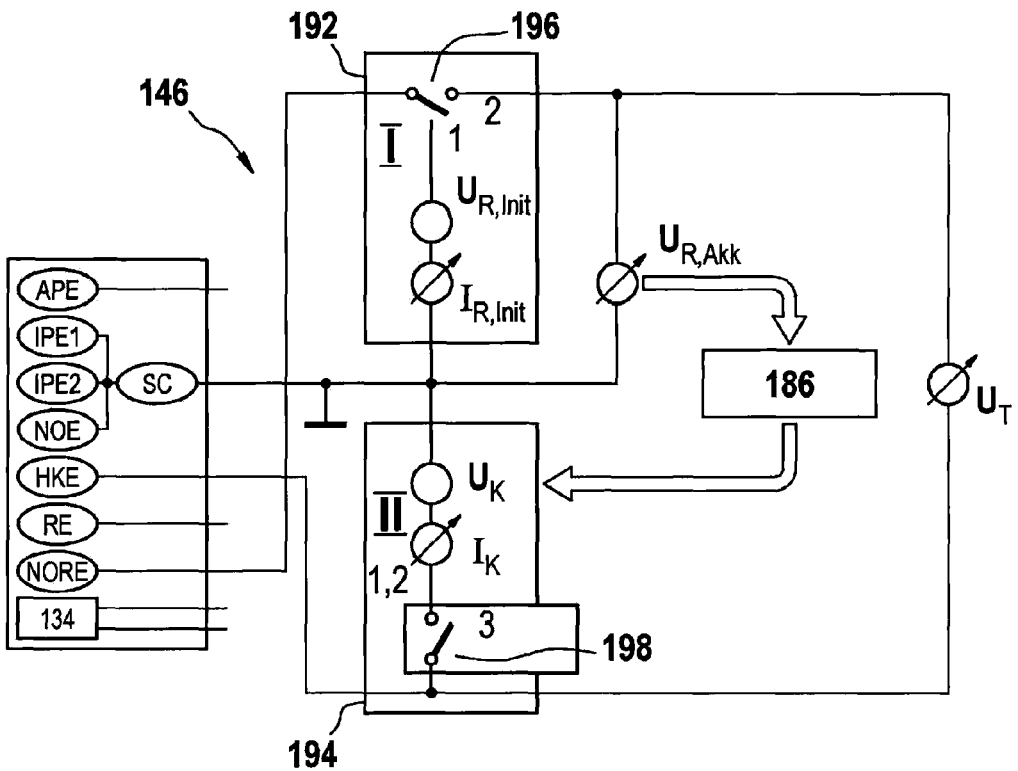

FIGS. 11A and 11B illustrate once again, as extracts, those components of controller 146, acting as an operating and evaluating unit, that are responsible for the actual NO measurement. FIG. 11A shows Variant 1 already shown in FIG. 10, whereas FIG. 11B shows a Variant 2 which makes possible an additional measurement of a voltage variation between hollow-chamber electrode HKE and NO reference electrode NORE. In both variants, upper combination element 192 implements the voltage impression $U_{R, Init}$ in the initialization phase. In that initialization phase, emptying, for example, of gas-tight chamber 148 takes place (compare FIGS. 8 and 9) which, for example, may be performed by switch position I/1. In addition, upper combination element 192 implements maintenance of the limit current between NOE and NORE, for example by a positive pumping voltage in relation to NOE. At the same time, in the case of a short-circuit ($U_K=0$ V) of voltage source $U_K$ in first combination element 192 (switch position II/1,2), the same pumping voltage from first combination element 192 is applied between HKE and NORE and hence the oxygen that accumulated in the preceding phase is also pumped out of gas-tight chamber 148 acting as an accumulation chamber, especially by a positive pumping voltage between HKE and NORE in relation to NOE-HKE, and hence gas-tight chamber 148 is emptied. The associated total current or total charge is determined in first combination element 192 and the chamber current or proportion of the charge is determined in second combination element 194 by the current-measuring devices. From this it is also possible to determine, by subtraction, the proportion of the charge arising from the limit current via NOE-NORE. Those additional measured variables are used in the so-called multiple-variable evaluation.

In a further embodiment, the connection of NOE may be continuously set for voltage measurement (such as switch position 2 in first combination element 192) and, instead of the switch-over, only a switching-on of the pumping voltage $U_{R, Init}$ (switch position 1) may be carried out. Thus, in the initialization phase, in the case of $U_{R, Init}=U_{R, Acc,setpoint}$, the manipulated value $U_K=0$ V (short-circuit between HKE and NOE) is given automatically via closed-looped controller 186. Otherwise, closed-loop controller 186 must be disconnected and/or stopped in the initialization phase, and the manipulated value must be set to 0 V.

In the actual accumulation phase (Phase II, switch position I/2 and II/1,2), by voltage impression $U_K$ the NO limit current is pumped from NOE to HKE into gas-tight chamber 148 (positive voltage in relation to NOE). Corresponding to switch position 2 of first combination element 192 (I/2), the voltage between NOE and NORE is continuously determined by the voltage measurement $U_{R, Acc}$. The pumping voltage for filling gas-tight chamber 148 is varied by closed-loop controller 186 in such a way that a defined voltage (for example $U_{R, Acc}=450$ mV) is continuously established between NOE and NORE. Measurement of the state of the chamber by way of the variation of the chamber voltage (HKE-NORE, analogously to FIG. 6 with chamber voltage HKE2-LR) is carried out in accordance with Variant 2 of the evaluating circuit by an additional measurement of voltage $U_T$ between HKE and NORE. In this case, in accordance with the foregoing remarks, the time interval until attainment of a defined voltage threshold is evaluated as a sensor signal (compare FIG. 6 and the relevant description). In a further simplification of the evaluating circuit in accordance with Variant 1 (FIG. 11A), that additional voltage measurement may be dispensed with since, with sufficiently accurate and rapid closed-loop control, the chamber voltage also may be determined from the manipulated variable. In accordance with the mesh equation, the manipulated variable differs at each point in time from the actually sought voltage between chamber electrode HKE and NO reference electrode NORE only by the constant value of the control variable (for example 450 mV). Accordingly, the manipulated value also may be used directly as a sensor signal.

Optionally shown switch 198 (switch position 3 in the accumulation phase) in second combination element 194 enables simple in situ calibration of the accumulation cell to be performed. Since, in this case, no active filling of gas-tight chamber 148 is carried out, this allows, for example, a zero balancing of gas-tight chamber 148, for example by chamber filling taking place merely as a result of parasitic effects such as electronic leakage currents. Alternatively, in situ calibration may also be carried out without the use of switch 198, by a comparison of the charge quantity in the accumulation phase (chamber filling) and the charge quantity upon subsequent emptying of the chamber (initialization).

Figure 12:
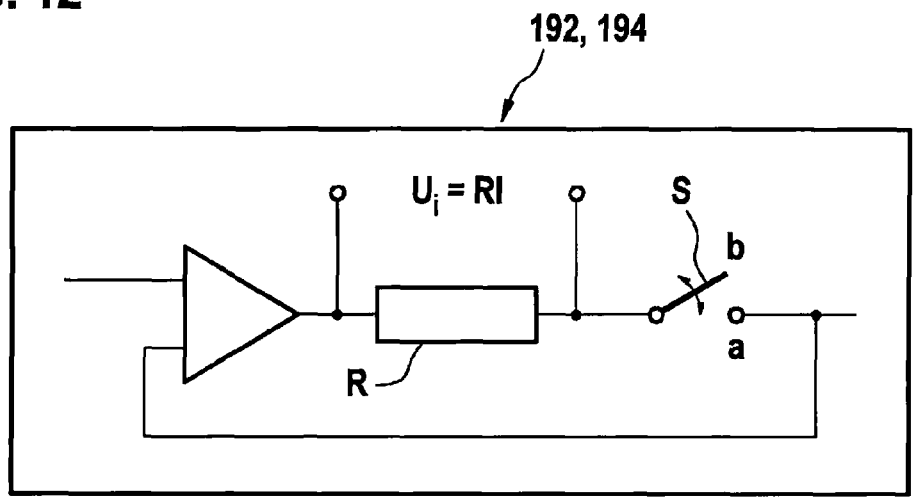
FIGS. 12 and 13 show different configurations of combination elements for use in a controller of a device according to the present invention.
Figure 13:
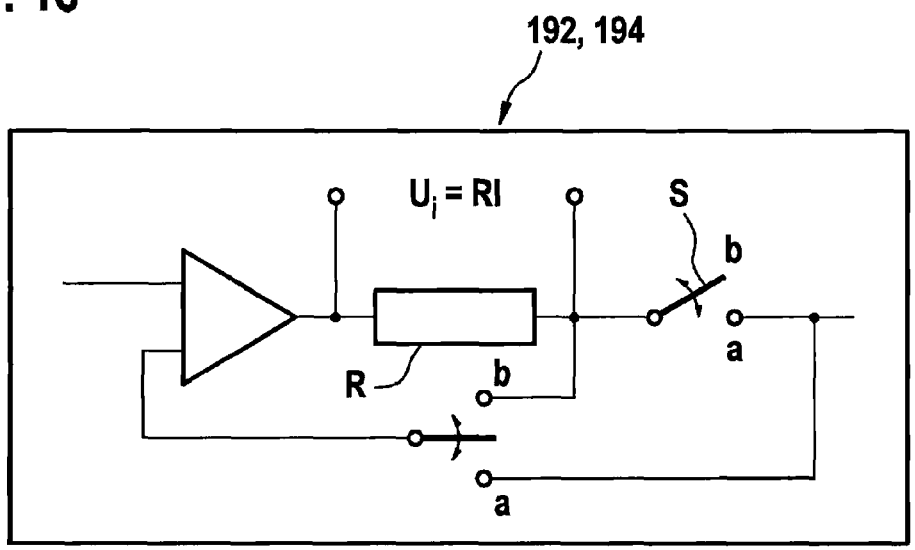

For implementation of combination elements 192, 193, various variants are possible. By way of example, two such variants of combination elements 192, 194 are illustrated in FIGS. 12 and 13. In both cases, a voltage source, simultaneous current measurement via a shunt resistor R (the associated shunt voltage source is not shown) and a switch S are integrated. The advantage of this form of voltage source resides in the fact that, in accordance with the feedback circuit of the impedance converter, the voltage drop across shunt resistor R and the voltage drop across switch S are intrinsically compensated for and do not affect the output voltage. In contrast to Variant 1 illustrated in FIG. 12, in which disturbances (for example voltage and/or current peaks in the switch-over operation, that is, when the feedback circuit is switched on again b→a) could possibly occur, those disturbances are prevented by the circuitry according to Variant 2 shown in FIG. 13 by virtue of the fact that the feedback circuit is also closed in switch position b. In addition, that Variant 2 also permits a possibility of balancing the current measurement or the voltage source since, with the output voltage of the overall system switched off (switch position b), for a given voltage at the input of the impedance converter a defined current flows across shunt resistor R. Thus, depending on the input voltage, both a zero balancing and a balancing of further defined currents are possible. That concept may also be used in principle in a conventional limit current sensor.

As a third variant, it would furthermore be possible to lead back the feedback circuit upstream of switch S and thereby avoid a switching process in the feedback circuit. However, in the case of this variant, an undesired voltage drop across switch S, which is not an ideal switch as a rule, and a slight distortion of the output voltage may occur.

Figure 14:
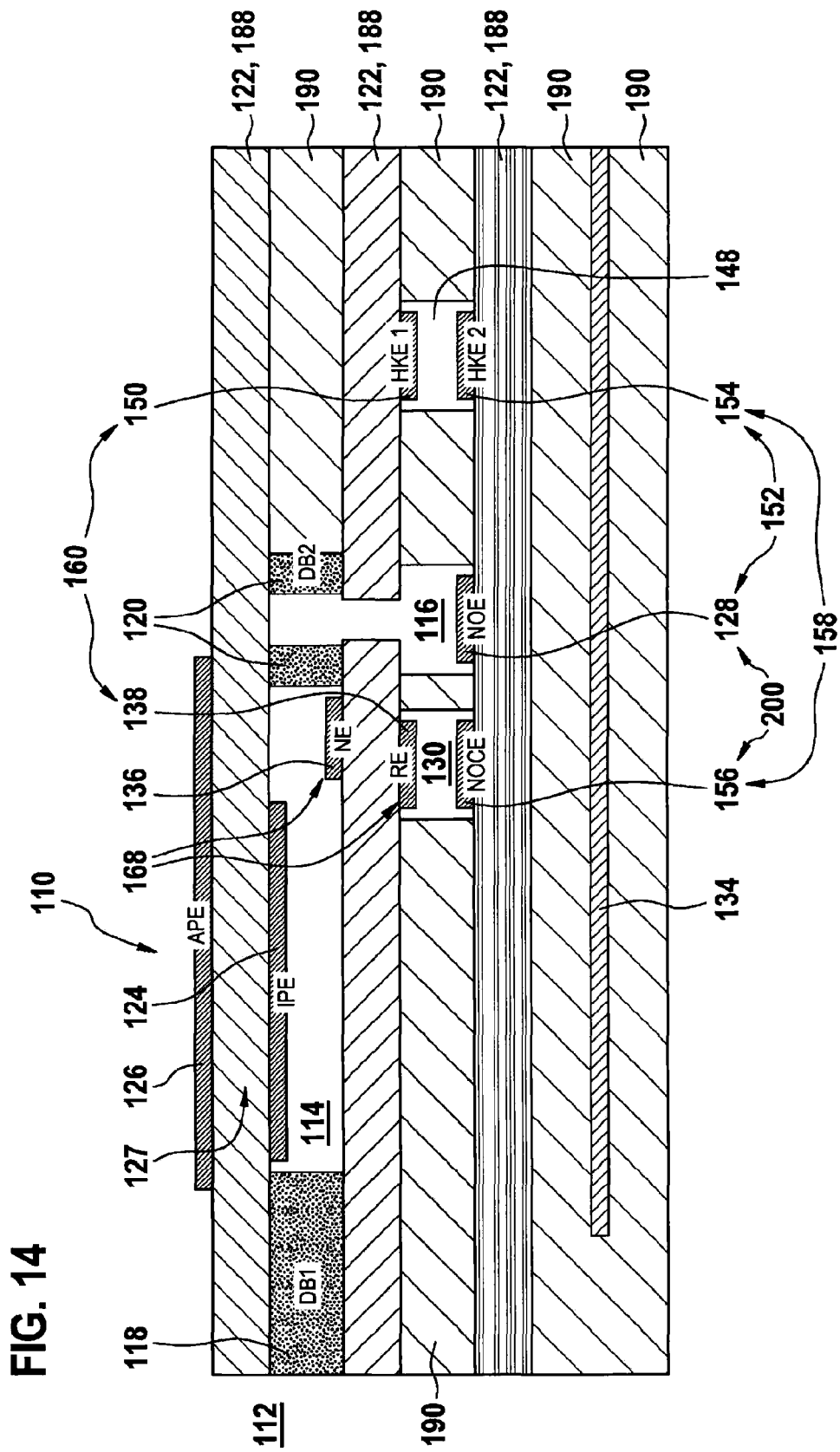
FIG. 14 shows a modification of the sensor element shown in FIG. 8.

In FIG. 14, a modification of sensor elements 110 shown in FIGS. 8 and 9 is illustrated, which modification may also be used in a device 144 according to the present invention. In this case, once again a reference gas space is provided which, for example, may be in the form of reference air duct 130. Alternatively, as described above, that reference gas space may in principle be in a different form, for example in the form of a closed reference gas space, for example a pumped reference, in which a defined gas atmosphere, for example a defined air ratio, is established by a pumping operation. Various forms are possible.

The exemplary embodiment illustrated in FIG. 14 substantially corresponds to the exemplary embodiment illustrated in FIG. 8. In contrast to FIG. 8, however, FIG. 14 again shows, for example, an end-face gas inlet via first diffusion barrier 118. Alternatively or in addition, however, a gas inlet bore 166 could again be used analogously to FIG. 8. In addition, in the arrangement shown in FIG. 14, two electrodes are again provided inside the reference gas space, for example inside reference air duct 130. Thus, an oxygen reduction reference electrode 138 designated RE is provided which, together with oxygen reduction measuring electrode 136 designated NE in first chamber 114, is able to form an oxygen reduction measuring cell 168. Furthermore, that electrode RE is able to form together with an electrode HKE I 150 disposed in the gas-tight chamber a measuring cell 160. In addition, a further electrode 156, designated NOCE in FIG. 14, is provided in the reference gas space, for example in reference air duct 130. That further electrode is able to form together with an electrode disposed in gas-tight chamber 148—in this case, by way of example, a second hollow-chamber electrode 154 (designated HKE II)—an initialization pumping cell 158. Furthermore, HKE II is able to form with a first pumping electrode 128, designated NOE here and disposed in second chamber 116, a pumping cell 152.

Once again, solid electrolytes 122 in the form of solid electrolytes 122 are in the form of solid electrolyte layers 188 which are separated from one another by ionically non-conductive isolator layers 190, for example once again by aluminum oxide layers. In that manner, the following groups of electrochemical cells galvanically isolated from one another are formed:
group 1: oxygen reduction pumping cell 127,
group 2: oxygen reduction measuring cell 168 and measuring cell 160,
group 3: initialization pumping cell 158 and pumping cell 152.

Once again, one electrode each of a cell from each group may be electrically combined, for example to form a shared connection, analogously to the constructions in FIGS. 10 and 11A and 11B.

Electrodes NOE and NOCE may furthermore form together a NOx cell which is identified by reference numeral 200 in FIG. 14. With that NOx cell it is possible to implement, for example, a conventional NOx measuring principle. That NOx cell 200 also could be assigned to the third group mentioned above. The NOCE is located in this case in reference air duct 130 or in another reference gas space. As described above, the electrodes may be constructed in general as cermet electrodes. The supply lines to the connection pads may be in the form of separate or partially combined metal layers.

Regarding the measuring principle of sensor element 110 illustrated in FIG. 14 reference may be made, for example, to the foregoing description. For example, in the case of oxygen-rich exhaust gas, oxygen may be continuously removed electrochemically from first chamber 114 via oxygen reduction pumping cell 127, and more specifically, for example, until there is a predefined voltage, for example a voltage of 400 mV, at oxygen reduction measuring cell 168. The potential of APE 126 is then normally more positive than the potential of IPE 124. The oxygen diffusion current then continues as an electrically measurable pumping current at electrodes IPE and APE and may be used as a measured variable for the oxygen content in the exhaust gas. In the case of exhaust gas with an oxygen deficit, the pumping direction through oxygen reduction measuring cell 127 is normally reversed in this exemplary embodiment or other exemplary embodiments. The potential of APE 126 is then normally more negative than that of IPE 124. To regulate the APE potential it is possible to use, for example, a closed-loop control system whose input variable is formed by the voltage of oxygen reduction measuring cell 168. In the exemplary embodiment shown in FIG. 14, as in other preferred exemplary embodiments of the present invention, oxygen reduction measuring cell 168 and oxygen reduction pumping cell 127 are galvanically isolated from each other.

By electrochemical pumping, the oxygen partial pressure in first chamber 114 is preferably kept constant. IPE 124 is in this case preferably less catalytically active than a pure platinum-cermet electrode, for example by admixture of gold with a platinum-cermet electrode. Nitrogen oxides are able to pass over that IPE 124 preferably virtually unchanged and pass via second diffusion barrier 120 into second chamber 116. In second chamber 116, NOx is catalytically decomposed at NOE, which may, for example, be in the form of a platinum-rhodium-cermet electrode, and the resulting oxygen is electrochemically removed via electrode NOE (NOx electrode). The pumping current that develops, which is able to flow, for example, via NOx cell 200, may accordingly already be used as a first measure of the nitrogen oxide concentration.

As an alternative or in addition, the method described above may be used. Thus, the resulting oxygen may be pumped in an accumulation phase (also referred to hereinafter, without limitation of other possible sequences, as phase I) into gas-tight chamber 148 and stored therein. In an initialization phase (also referred to hereinafter, without limitation of other possible time sequences, as phase II), oxygen may be pumped out of gas-tight chamber 148 into reference air duct 130 and/or into first chamber 114, it being possible for that gas-tight chamber 148 to be simultaneously emptied. HKE I and HKE II are disposed in gas-tight chamber 148 on different solid electrolyte layers 188.

Figure 15:
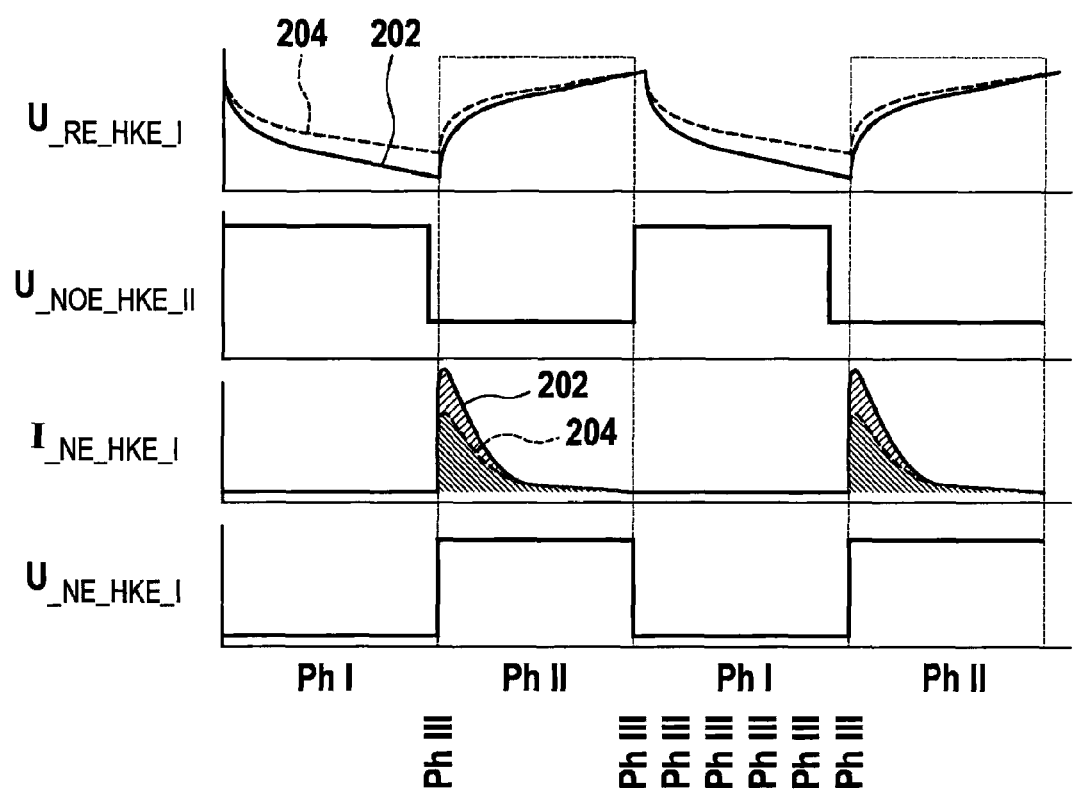
FIG. 15 shows a schematic representation of voltage and current variations during an exemplary embodiment of a method according to the present invention.

In a third phase (also referred to hereinafter, without limitation of further possible sequences, as phase III), which may also be completely or partially combined with the above-described initialization phase and/or accumulation phase, electrode pair HKE I and RE may be used to measure the Nernst voltage and hence the oxygen partial pressure in gas-tight chamber 148. For example, the Nernst voltage may be proportional to the logarithm of the partial pressure ratio between gas-tight chamber 148 and reference air duct 130 or the reference gas space constructed in a different manner. The resulting Nernst voltage over time in the third phase and/or the pumping current in the second phase may be evaluated as a measure of the NOx concentration and may control the transition between the phases. The first and the second phase may constantly alternate whereas the third phase may, for example, either repeatedly interrupt the first phase or form the transition between the first and the second phase. This is shown by way of example in FIG. 15. Therein, the first phase is designated Ph I, the second phase Ph II and the third phase Ph III. Various voltage and current variations between the electrodes named in the indices on the vertical axis are illustrated. In the topmost illustration, therefore, the voltage between electrodes RE and HKE I as a function of time is shown, in the second illustration from the top the voltage between NOE and HKE II, in the third illustration from the top the current between NE and HKE I and, in the fourth, lowermost illustration, the voltage between NE and HKE I. The horizontal axis represents the time axis. Curves 202 indicate the variation for a higher NOx concentration, and curves 204 the variation for a low NOx concentration.

In the example method, a number of signals, for example, may be evaluated. For example, it is possible to evaluate the current integral in phase II on pumping gas-tight chamber 148 empty. As an alternative or in addition, the voltage between HKE I and RE may be evaluated. Again as an alternative or in addition, the continuous pumping current of NOCE may be evaluated. The use of the accumulating method also leads, by virtue of its time integration of the NOx concentration, to a great improvement in accuracy. The interference of the mentioned cells with one another is prevented by the galvanic isolation by isolator layers 190. It certainly also makes possible, as already mentioned above, the shared connection of some electrodes such as, for example, IPE, NE and NOE.

As described above, the layered structure illustrated in FIG. 14 or a different layered structure of a sensor element 110 according to the present invention may be realized in various ways for use in a device 144 according to the present invention. For example, isolation layers 190 and solid electrolyte layers 188 may be produced by films laminated to one another. As an alternative or in addition, screen printed layers may also be used. The use of isolation layers 190 also has further advantages beyond that. For example, those isolation layers 190 also help to ensure, in the described accumulating principle, in which a gas-tight chamber 148 is used, that stored gas is not lost from gas-tight chamber 148 to too great an extent owing to leakage currents or electronic residual conductivity.

FIGS. 16 to 20 illustrate further forms of sensor element 110 that may be employed in a device 144 according to the present invention, for example in the device shown in FIG. 10. Alternatively, however, other controllers 146 may be used. Regarding the functions of the individual elements of sensor elements 110 reference may largely be made to the foregoing description. In addition, FIGS. 16 to 20 indicate by way of example electrode contacts 206 and supply lines 208; however, other forms of those electrode contacts 206 and supply lines 208 are also possible.

Figure 16:
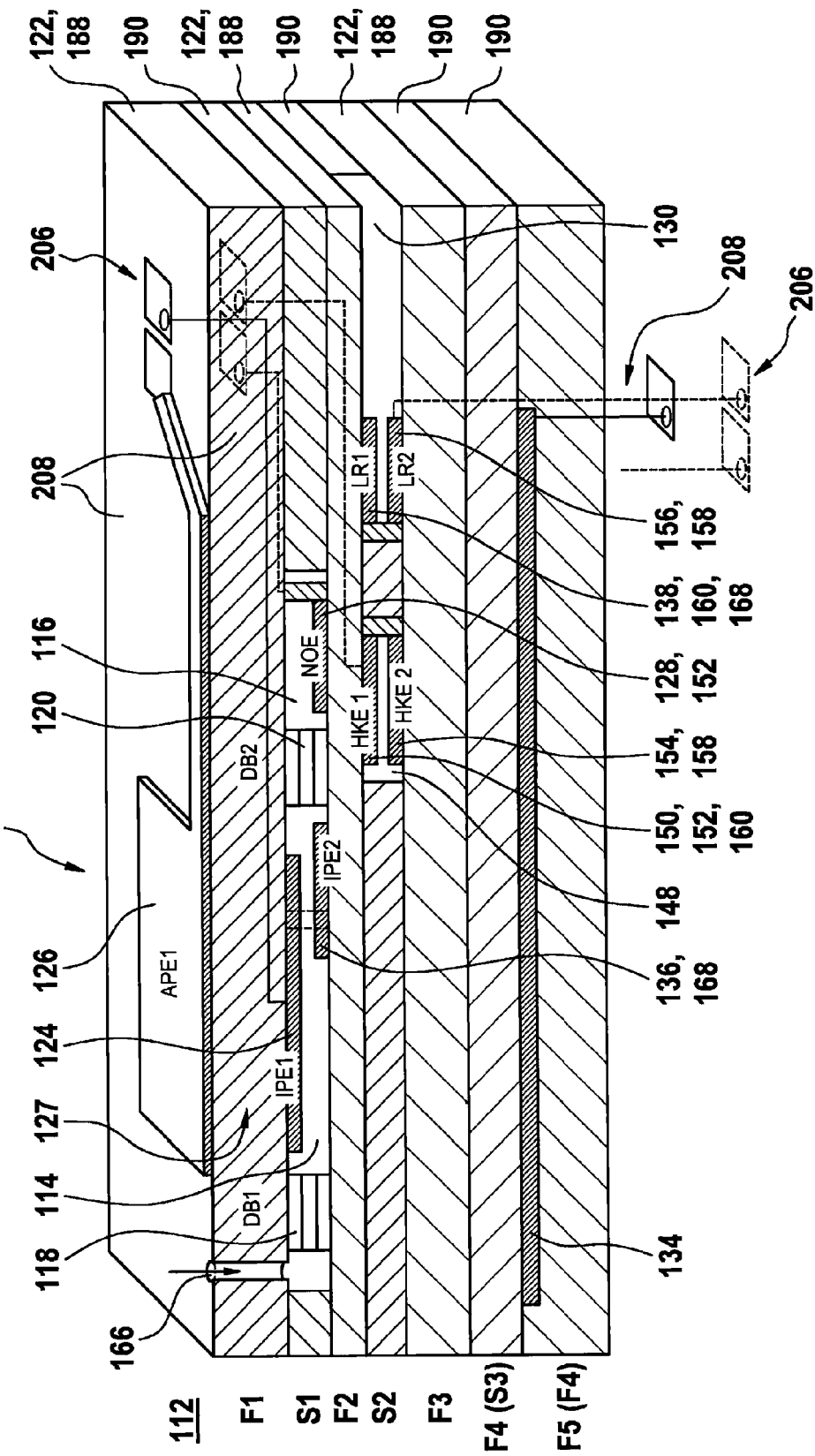
FIGS. 16 to 20 show various alternative constructions of sensor elements for use in a device according to the present invention.

FIG. 16 illustrates an exemplary embodiment in which two hollow-chamber electrodes HKE I and HKE II are provided, which may also be electrically connected to each other, as indicated in FIG. 16. A reference air duct 130 and/or a different kind of reference air space is further provided, there being disposed in reference air duct 130 two electrodes 138, 156 which, however, may also be completely or partially electrically connected to each other, as indicated in FIG. 16. Once again, galvanic isolation of the cells is carried out, so that supply lines 208 may be completely or partially combined. A total of seven electrodes and two heater contacts thus results in seven supply lines 208 and seven electrode contacts 206. In FIG. 16, as in subsequent Figures also, a distinction is optionally to be made with regard to isolator layers 190 between two types of isolator layer, namely, for example, between an aluminum oxide film, as may be used, for example, for isolator layer F5 which may also be completely or partially combined with isolator layer F4, and layers constructed in a different manner, for example printed AlOx layers, as may be used, for example, for isolator layers S1, S2 and optionally S3 in FIG. 16 or also in the other Figures. Other constructions are, however, also possible in principle.

Figure 17:
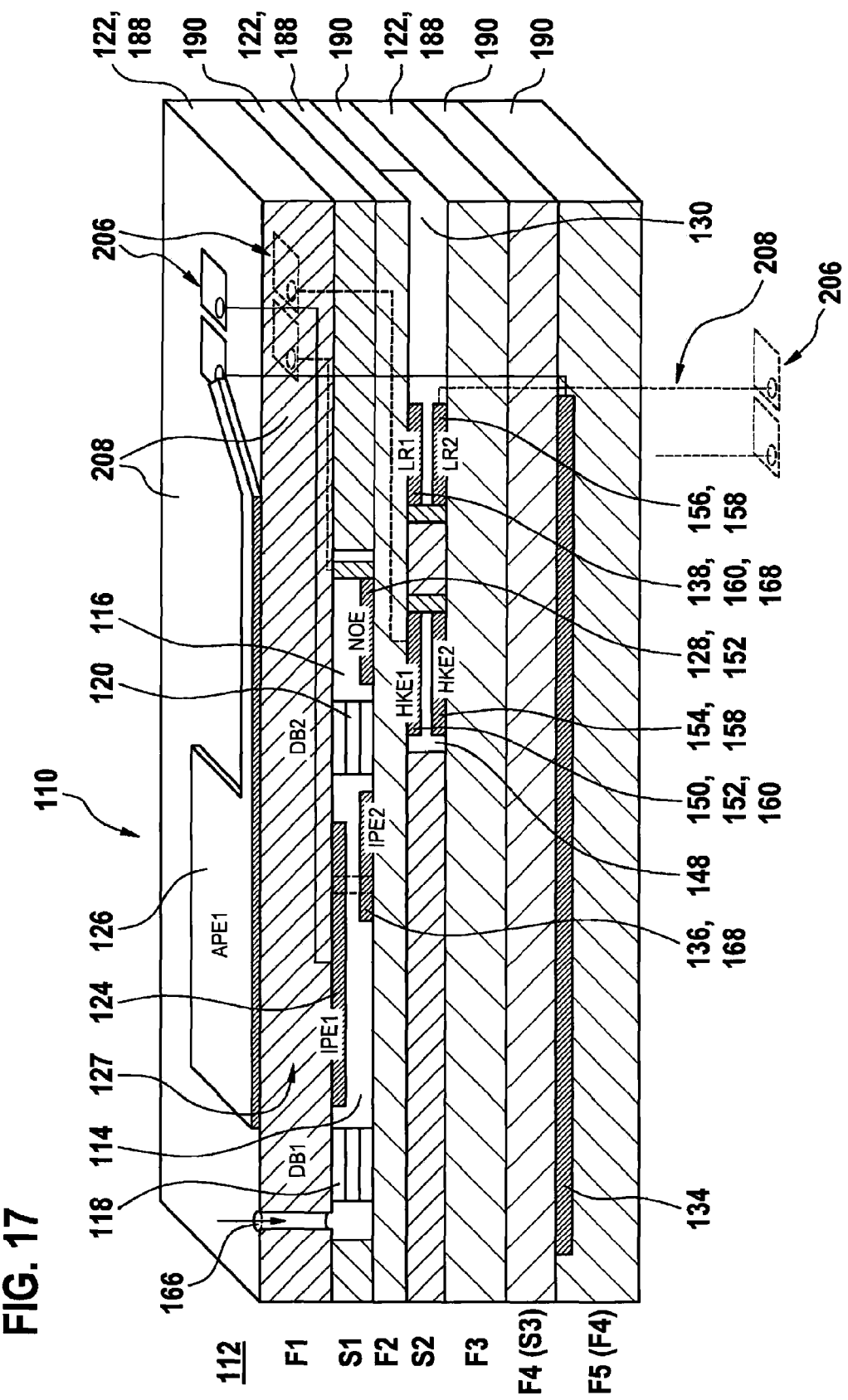
Figure 18:
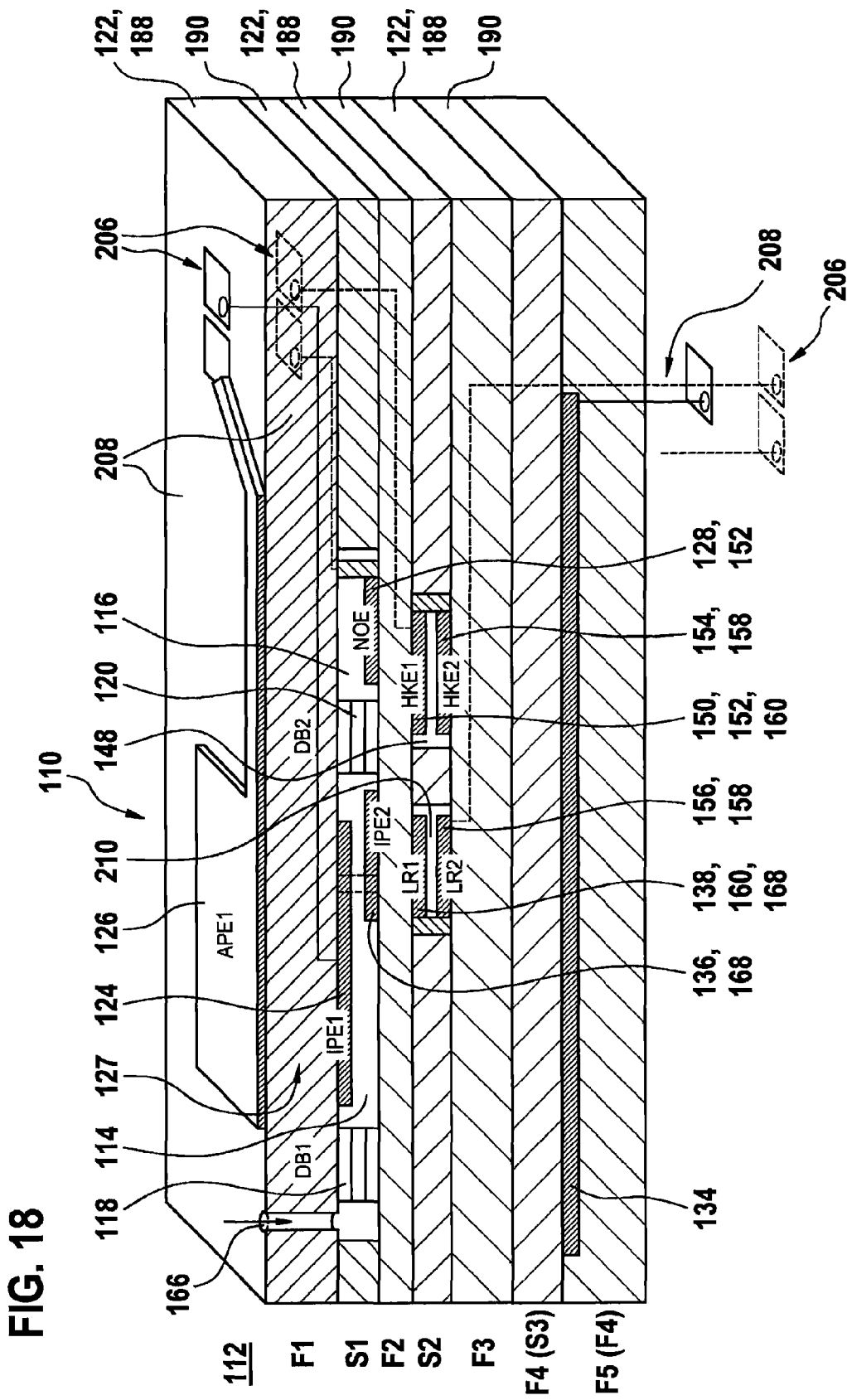

FIG. 17 illustrates an exemplary embodiment of a sensor element 110 in which once again two hollow-chamber electrodes HKE I and HKE II may be used and in which once again two electrodes 138, 156 may be provided in the reference gas space, for example in reference air duct 130. Those electrodes HKE I and HKE II and LR I and LR II may again, as indicated in FIG. 17, be completely or partially electrically connected to each other so that once again they may be contacted, for example, via a shared supply line 208. As indicated in FIG. 17, one of supply lines 208 to heating element 134 is connected to supply line 208 to APE I. A further heater contact remains, therefore, which may be routed, for example, over the underside of sensor element 110 in FIG. 17. A total of seven electrodes and one heater contact thus results in six supply lines 208 and a corresponding number of electrode contacts 206. In FIG. 18, a further modification of the sensor element shown in FIG. 16 is shown by way of example. Instead of reference air duct 130, a different kind of reference gas space is used, in this case, for example, a closed reference gas space which may be constructed, for example, as pumped reference 210. Otherwise, reference may be made to the construction shown in FIG. 16. A total of seven electrodes and two heater contacts therefore results in a total of seven supply lines 208 and seven electrode contacts 206.

Figure 19:
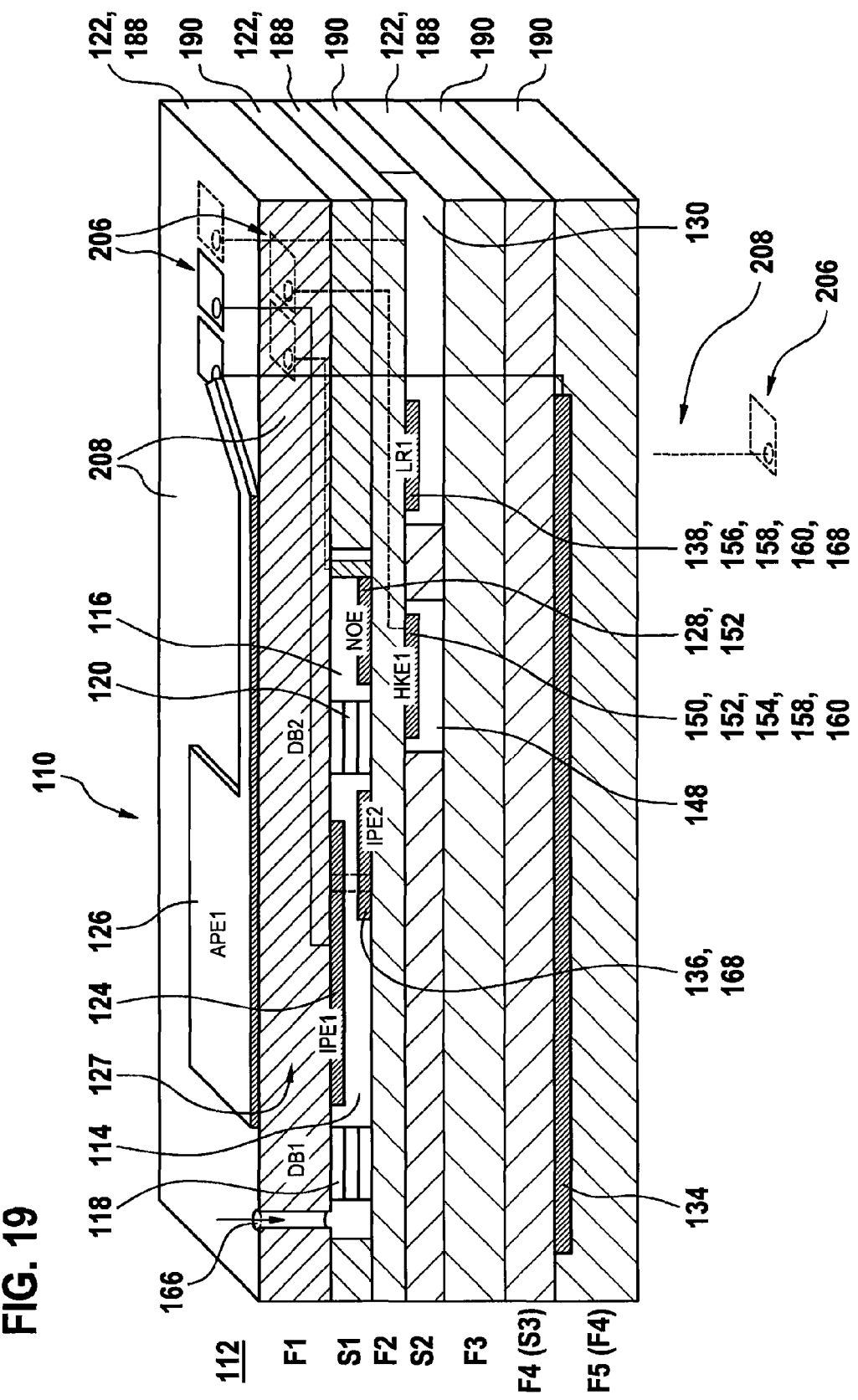

FIG. 19 illustrates an exemplary embodiment in which only one electrode is provided in gas-tight chamber 148, which electrode is at the same time able to fulfill the functions of electrodes 150 and 154 and is designated HKE I in FIG. 19. In addition, once again a reference air duct 130 is provided in which similarly only one electrode is provided, which is designated LR I in FIG. 19 and which assumes the function of electrodes 138 and 156. HKE I and LR I are disposed on a solid electrolyte layer 188 which is designated F II in FIG. 19 and on which NOE 128 is also disposed. A further solid electrolyte layer 188 lying therebeneath, which is designated F III, may therefore be optionally omitted in FIG. 19 and/or may be replaced by a further isolator layer 190. In addition, one of the contacts of heating element 134 in FIG. 19 is again connected, analogously to FIG. 17, to the supply line to APE I. Thus, a total of seven electrodes and an additional heater contact results in only six supply lines 208 and six electrode contacts 206.

Figure 20:
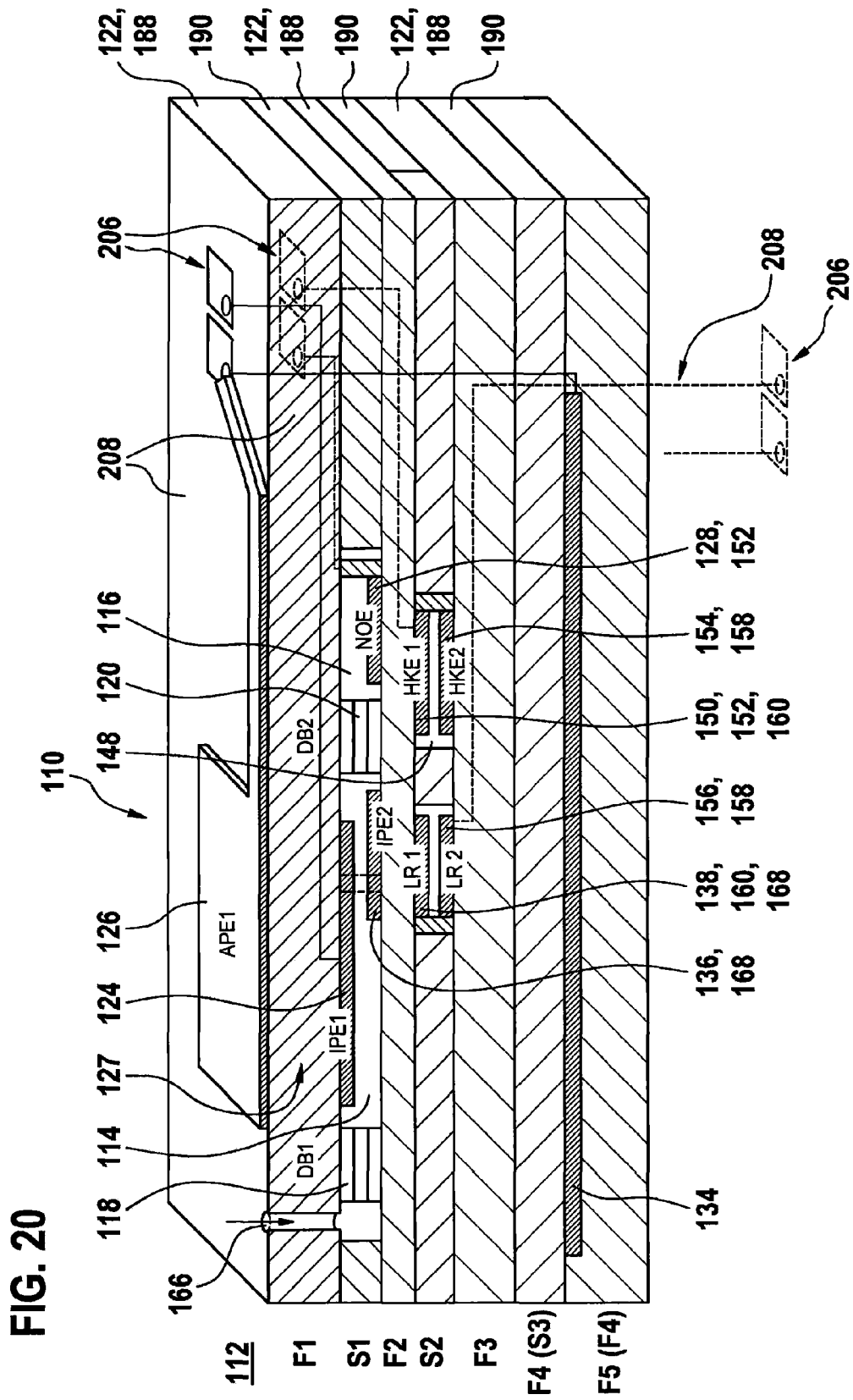

Finally, FIG. 20 illustrates an exemplary embodiment of a sensor element 110, which may in the first place largely correspond to the exemplary embodiment in FIG. 18. Once again, a reference gas space in the form of a pumped reference 210, for example, may also be provided here. In addition, a heater contact of heating element 134 may again be combined with one of the supply lines to APE I, as is also indicated in FIG. 20. Seven electrodes and an additional heater contact thus result in a total of six supply lines 208 and six electrode contacts 206.

What is claimed is:

1. A method for detecting a proportion of at least one gas species in a measurement gas space using at least one sensor element, the sensor element having at least one oxygen reduction pumping cell for concentration of the gas species, at least one pumping cell connected downstream of the oxygen reduction pumping cell, at least two pumping electrodes, and at least one gas-tight chamber, wherein at least one of the pumping electrodes may be exposed to gas from the measurement gas space which has been concentrated by the oxygen reduction pumping cell, at least a further one of the pumping electrodes is disposed in the gas-tight chamber, and at least one measuring electrode is disposed in the gas-tight chamber, the oxygen reduction pumping cell and the pumping cell being galvanically isolated by at least one isolator layer such that ion transport between the oxygen reduction pumping cell and the pumping cell is eliminated, the method comprising:

carrying out an initialization phase, wherein in the initialization phase, a defined initial state in the gas-tight chamber is carried out by pumping;

carrying out an accumulation phase, wherein in the accumulation phase, an accumulation of a quantity of oxygen in the gas-tight chamber is carried out by pumping via the pumping cell, the quantity of oxygen representing a measure of a proportion of the gas species in the measurement gas; and determining the proportion of the gas species from a potential variation of the measuring electrode.

2. The method as recited in claim 1, further comprising:
detecting the potential variation of the potential of the measuring electrode using a potential difference between the measuring electrode and at least one reference electrode.

3. A device for detecting a proportion of at least one gas species in a measurement gas space, comprising:
at least one sensor element having at least one oxygen reduction pumping cell for reduction of the gas species, at least one pumping cell connected downstream of the oxygen reduction pumping cell, at least two pumping electrodes, and at least one gas-tight chamber, at least one of the pumping electrodes may be exposed to gas from the measurement gas space which has been concentrated by the oxygen reduction pumping cell, and at least a further one of the pumping electrodes is disposed in the gas-tight chamber, at least one measuring electrode is disposed in the gas-tight chamber, and wherein the oxygen reduction pumping cell and the pumping cell are galvanically isolated by at least one isolator layer such that ion transport between the oxygen reduction pumping cell and the pumping cell is eliminated.

4. The device as recited in claim 3, further comprising:
at least one controller configured: i) to carry out an initialization phase, wherein in the initialization phase, a defined initial state in the gas-tight chamber is carried out by pumping, ii) to carry out an accumulation phase, wherein in the accumulation phase, an accumulation of a quantity of oxygen in the gas-tight chamber is carried out by pumping via the pumping cell, the quantity of oxygen representing a measure of a proportion of the gas species in the measurement gas, and iii) to determine the proportion of the gas species from a potential variation of the measuring electrode.

5. The device as recited in claim 3, wherein the sensor element includes at least one chamber for concentration of the gas species, and wherein at least one inner pumping electrode of the oxygen reduction pumping cell is disposed in the chamber.

6. The device as recited in claim 5, wherein the inner pumping electrode and the pumping electrode that may be exposed to the concentrated gas from the measurement gas space are electrically connected to each other.

7. The device as recited in claim 5, wherein at least one oxygen reduction measuring electrode is further provided in the chamber for concentration of the gas species, wherein the sensor element further includes at least one reference gas space, wherein at least one oxygen reduction reference electrode is provided in the reference gas space, wherein the oxygen reduction reference electrode and the oxygen reduction measuring electrode form at least one oxygen reduction measuring cell, and wherein the oxygen reduction measuring cell is galvanically isolated from the oxygen reduction pumping cell.

8. The device as recited in claim 7, wherein the oxygen reduction measuring cell is galvanically isolated from the pumping cell.

9. The device as recited in claim 8, wherein the oxygen reduction measuring electrode is electrically connected to at least one of (i) the inner pumping electrode of the oxygen reduction pumping cell, and (ii) the pumping electrode that may be exposed to the concentrated gas from the measurement gas space.

10. The device as recited in claim 3, wherein the oxygen reduction pumping cell and the pumping cell each have solid electrolyte layers that are completely isolated with respect to one another by the at least one isolator layer which is interposed between two solid electrolyte layers to provide the galvanic isolation between the oxygen reduction pumping cell and the pumping cell.

11. The device as recited in claim 3, wherein the sensor element further includes at least one reference gas space, at least one reference electrode being provided in the reference gas space, the reference electrode forms with the measuring electrode a measuring cell, and wherein the measuring cell is galvanically isolated from the oxygen reduction pumping cell.

* * * * *